US012193435B2

(12) United States Patent
Lidor-Nili et al.

(10) Patent No.: US 12,193,435 B2
(45) **Date of Patent: *Jan. 14, 2025**

(54) **METHODS OF CONTROLLING WEED OF THE *AMARANTH* GENUS**

(71) Applicant: Weedout Ltd., Nes Ziona (IL)

(72) Inventors: Efrat Lidor-Nili, Nes Ziona (IL); Orly Noivirt-Brik, Givataim (IL); Ido Shwartz, Herzeliya (IL); Herve Huet, Yehud (IL)

(73) Assignee: Weedout Ltd., Nes Ziona (IL)

( * ) Notice: Subject to any disclaimer, the term of this patent is extended or adjusted under 35 U.S.C. 154(b) by 0 days.

This patent is subject to a terminal disclaimer.

(21) Appl. No.: 18/385,412

(22) Filed: Oct. 31, 2023

(65) Prior Publication Data

US 2024/0057586 A1 Feb. 22, 2024

Related U.S. Application Data

(62) Division of application No. 17/052,834, filed as application No. PCT/IB2019/053688 on May 6, 2019, now Pat. No. 11,812,735.

(60) Provisional application No. 62/667,521, filed on May 6, 2018.

(51) Int. Cl.
*A01M 99/00* (2006.01)
*A01H 1/02* (2006.01)

(52) U.S. Cl.
CPC ............... *A01M 99/00* (2013.01); *A01H 1/02* (2013.01)

(58) Field of Classification Search
CPC ................................ A01H 1/02; A01M 99/00
See application file for complete search history.

(56) References Cited

U.S. PATENT DOCUMENTS

| | | | |
|---|---|---|---|
| 8,437,498 | B2 | 5/2013 | Malsam |
| 11,369,116 | B2 | 6/2022 | Lidor-Nili et al. |
| 11,957,097 | B2 | 4/2024 | Shwartz et al. |
| 2006/0053686 | A1 | 3/2006 | Halwas |
| 2017/0042102 | A1 | 2/2017 | Safreno |
| 2017/0359943 | A1 | 12/2017 | Calleija et al. |
| 2018/0065749 | A1 | 3/2018 | Cantrell |
| 2019/0208790 | A1 | 7/2019 | Lidor-Nili et al. |
| 2020/0275617 | A1 | 9/2020 | Fabijanski et al. |
| 2020/0281139 | A1 | 9/2020 | Noivirt-Brik et al. |
| 2020/0288656 | A1 | 9/2020 | Lidor-Nili et al. |
| 2020/0288657 | A1 | 9/2020 | Novirt-Brik et al. |
| 2021/0068335 | A1 | 3/2021 | Noivirt-Brik et al. |
| 2021/0127610 | A1 | 5/2021 | Lidor-Nili et al. |
| 2021/0315176 | A1 | 10/2021 | Shwartz et al. |
| 2022/0279798 | A1 | 9/2022 | Lidor-Nili et al. |

FOREIGN PATENT DOCUMENTS

| | | |
|---|---|---|
| CN | 1395823 | 2/2003 |
| CN | 101536671 | 9/2009 |
| CN | 102106253 | 6/2011 |
| CN | 103782902 | 5/2014 |
| FR | 2933842 | 1/2010 |
| WO | WO 2014/085774 | 6/2014 |
| WO | WO 2015/164805 | 10/2015 |
| WO | WO 2016/191825 | 12/2016 |
| WO | WO 2017/194399 | 11/2017 |
| WO | WO 2017/203519 | 11/2017 |
| WO | WO 2007/093444 | 7/2018 |
| WO | WO 2019/106666 | 6/2019 |
| WO | WO 2019/106667 | 6/2019 |
| WO | WO 2019/106668 | 6/2019 |
| WO | WO 2019/215581 | 11/2019 |
| WO | WO 2019/215582 | 11/2019 |
| WO | WO 2020/084586 | 4/2020 |
| WO | WO 2020/084586 A9 | 10/2020 |

OTHER PUBLICATIONS

Peixe et al. "Gamma-irradiated pollen induces the formation of 2n endosperm and abnormal embryo development in European plum (*Prunus domestica* L., cv. "Rainha Claudia Verde")," Scientia Horticulturae 86 (2000) 267-278.*

Andreichenko et al. "Possibility of Regulating Seed Formation During Pollination with Mixed Pollen Containing Y-Irradiated Pollen," A.A. Bogomolets Kiev Medical Institute, vol. 315, No. 4, pp. 982-985, Dec. 1990.*

Feng et al. "Effect of enhanced ultraviolet-B radiation on pollen germination and tube growth of 19 taxa in vitro," Environmental and Experimental Botany 43 (2000) 45-53.*

Culpeper et al. "Glyphosphate-resistant Palmer amaranth (*Amaranthus palmeri*) confirmed in Georgia," Weed Science 54:620-626, 2006.*

Hansen "Precision pollination" Good Fruit Grower, Mar. 2016; https://www.goodfruit.com/precision-pollination/ Retrieved from the Internet, Feb. 2, 2023.*

Advisory Action Dated Mar. 1, 2022 From the US Patent and Trademark Office Re. U.S. Appl. No. 16/884,097. (11 Pages).

Clarifications Prior to Substantive Examination Dated Nov. 18, 2021 From the Instituto Nacional De La Propiedad Industrial Administracion Nacional De Patentes Argentina Re. Applicatiion No. P20170101373 together with English Summary. (6 Pages).

Communication Pursuant to Article 94(3) EPC Dated Dec. 2, 2022 From the European Patent Office Re. Application No. 17802323.0 with Claims. (7 Pages).

Communication Pursuant to Article 94(3) EPC Dated Aug. 12, 2021 From the European Patent Office Re. Application No. 17802323.0. (7 Pages).

Communication Pursuant to Article 94(3) EPC Dated Jul. 20, 2023 From the European Patent Office Re. Application No. 18883157.2 (5 Pages).

Communication Pursuant to Article 94(3) EPC Dated Nov. 20, 2020 From the European Patent Office Re. Application No. 17802323.0. (5 Pages).

(Continued)

*Primary Examiner* — Susan McCormick Ewoldt

(57) ABSTRACT

Methods of *Amaranthus* control are provided, comprising, artificially pollinating an *Amaranthus* species at a growth area with an effective amount of pollen that reduces fitness of the at least one *Amaranthus* species, the effective amount comprising 1 mg to 1 gram per plant per application using a precision tool-assisted application or 10 gram to 100 kg per acre per application using a non-precision tool-assisted application during a flowering season of the *Amaranthus* species.

4 Claims, No Drawings

(56) References Cited

OTHER PUBLICATIONS

Decision on Rejection Dated May 29, 2023 From the State Intellectual Property Office of the People's Republic of China Re. Application No. 201880086827.5. (4 Pages).
English Translation Dated Apr. 6, 2022 of Notification of Office Action and Search Report Dated Mar. 10, 2022 From the State Intellectual Property Office of the People's Republic of China Re. Application No. 201880086827.5. (4 Pages).
English Translation of Notification of Office Action Dated Jan. 25, 2022 From the State Intellectual Property Office of the People's Republic of China Re. Application No. 201780037868.0. (5 Pages).
Examination Report Dated Jan. 27, 2023 From the Australian Government, IP Australia Re. Application No. 2017271409. (5 Pages).
Examination Report Under Sections 12 & 13 of the Patents Act, 1970 and the Patents Rules, 2003 Dated Jul. 16, 2021 From the Government of India, Intellectual Property India, Patents, Designs, Trade Marks, Geographical Indications, The Patent Office Re. Application No. 201827046713. (7 Pages).
Final Official Action Dated Nov. 3, 2021 from the US Patent and Trademark Office Re. U.S. Appl. No. 16/884,097. (36 pages).
Final Official Action Dated Sep. 16, 2021 from the US Patent and Trademark Office Re. U.S. Appl. No. 16/304,145. (32 pages).
Final Official Action Dated Jul. 21, 2021 from the US Patent and Trademark Office Re. U.S. Appl. No. 17/053,089. (34 pages).
Final Official Action Dated Jun. 22, 2022 from US Patent and Trademark Office Re. U.S. Appl. No. 16/884,362. (32 pages).
Final Official Action Dated Jun. 30, 2022 from US Patent and Trademark Office Re. U.S. Appl. No. 16/885,311. (30 pages).
Hearing Notice Dated Jul. 3, 2023 From the Government of India, Intellectual Property India, The Patent Office Re. Application No. 201827046713. (2 Pages).
International Preliminary Report on Patentability Dated Dec. 6, 2018 From the International Bureau of WIPO Re. Application No. PCT/IL2017/050568. (8 Pages).
International Preliminary Report on Patentability Dated May 6, 2021 From the International Bureau of WIPO Re. Application No. PCT/IB2019/059171. (7 Pages).
International Preliminary Report on Patentability Dated Jun. 11, 2020 From the International Bureau of WIPO Re. Application No. PCT/IL2018/051301. (8 Pages).
International Preliminary Report on Patentability Dated Jun. 11, 2020 From the International Bureau of WIPO Re. Application No. PCT/IL2018/051302. (7 Pages).
International Preliminary Report on Patentability Dated Jun. 11, 2020 From the International Bureau of WIPO Re. Application No. PCT/IL2018/051303. (8 Pages).
International Preliminary Report on Patentability Dated Nov. 19, 2020 From the International Bureau of WIPO Re. Application No. PCT/IB2019/053688. (7 Pages).
International Search Report and the Written Opinion Dated Dec. 12, 2019 From the International Searching Authority Re. Application No. PCT/IB2019/059171. (9 Pages).
International Search Report and the Written Opinion Dated Aug. 14, 2019 From the International Searching Authority Re. Application No. PCT/IB2019/053690. (13 Pages).
International Search Report and the Written Opinion Dated Jul. 14, 2019 From the International Searching Authority Re. Application No. PCT/IB2019/053688. (10 Pages).
International Search Report and the Written Opinion Dated Feb. 21, 2019 From the International Searching Authority Re. Application No. PCT/IL2018/051301. (11 Pages).
International Search Report and the Written Opinion Dated Aug. 23, 2017 From the International Searching Authority Re. Application No. PCT/IL2017/050568. (11 Pages).
International Search Report and the Written Opinion Dated Feb. 24, 2019 From the International Searching Authority Re. Application No. PCT/IL2018/051302. (9 Pages).
International Search Report and the Written Opinion Dated Feb. 26, 2019 From the International Searching Authority Re. Application No. PCT/IL2018/051303. (11 Pages).
Interview Summary Dated Dec. 13, 2021 from US Patent and Trademark Office Re. U.S. Appl. No. 16/304,145. (2 pages).
Interview Summary Dated Oct. 20, 2023 from the US Patent and Trademark Office Re. U.S. Appl. No. 17/287,574. (3 pages).
Notice of Allowance Dated Jul. 6, 2023 from the US Patent and Trademark Office Re. U.S. Appl. No. 17/052,834. (18 pages).
Notice of Allowance Dated Feb. 9, 2022 from US Patent and Trademark Office Re. U.S. Appl. No. 16/304,145. (7 pages).
Notice of Allowance Dated Dec. 21, 2021 from US Patent and Trademark Office Re. U.S. Appl. No. 17/053,089. (12 pages).
Notification of Office Action and Search Report Dated Mar. 10, 2022 From the State Intellectual Property Office of the People's Republic of China Re. Application No. 201880086827.5. (25 Pages).
Notification of Office Action Dated Jul. 2, 2021 From the State Intellectual Property Office of the People's Republic of China Re. Application No. 201780037868.0 and Its English Summary. (6 Pages).
Notification of Office Action Dated Jan. 9, 2023 From the State Intellectual Property Office of the People's Republic of China Re. Application No. 201780037868.0. (4 Pages).
Notification of Office Action Dated Jun. 24, 2022 From the State Intellectual Property Office of the People's Republic of China Re. Application No. 201780037868.0 and Its Translation Into English. (10 Pages).
Notification of Office Action Dated Jan. 25, 2022 From the State Intellectual Property Office of the People's Republic of China Re. Application No. 201780037868.0 with an English Summary. (6 Pages).
Notification of Office Action Dated Dec. 28, 2022 From the China National Intellectual Property Administration Re. Application No. 201880086827.5. (5 Pages).
Office Action Dated Jul. 9, 2019 From the Israel Patent Office Re. Application No. 263232 and Its Translation Into English. (5 Pages).
Office Action Dated Dec. 10, 2020 From the Israel Patent Office Re. Application No. 263232 and Its Translation Into English. (9 Pages).
Office Action Dated Feb. 28, 2023 From the Israel Patent Office Re. Application No. 274978. (3 Pages).
Office Action Dated Mar. 31, 2022 From the Israel Patent Office Re. Application No. 263232 and Its Translation Into English. (6 Pages).
Official Action Dated Feb. 2, 2021 From the US Patent and Trademark Office Re. U.S. Appl. No. 16/884,097. (36 Pages).
Official Action Dated Feb. 9, 2023 from US Patent and Trademark Office Re. U.S. Appl. No. 17/052,834. (25 pages).
Official Action Dated Sep. 9, 2022 from US Patent and Trademark Office Re. U.S. Appl. No. 17/052,834. (65 pages).
Official Action Dated Feb. 17, 2021 From the US Patent and Trademark Office Re. U.S. Appl. No. 17/053,089. (45 Pages).
Official Action Dated Nov. 18, 2021 from the US Patent and Trademark Office Re. U.S. Appl. No. 16/884,362 (56 pages).
Official Action Dated Nov. 18, 2021 from the US Patent and Trademark Office Re. U.S. Appl. No. 16/885,311. (55 pages).
Official Action Dated May 23, 2023 from the US Patent and Trademark Office Re. U.S. Appl. No. 16/884,362. (20 pages).
Official Action Dated May 24, 2023 From the US Patent and Trademark Office Re. U.S. Appl. No. 17/287,574. (106 Pages).
Official Action Dated Dec. 30, 2020 from the US Patent and Trademark Office Re. U.S. Appl. No. 16/304,145. (37 pages).
Relatório de Busca e Parecer [Search Report and Written Opinion] Dated Sep. 19, 2022 From the Serviço Público Federal, Ministério da Economia, Instituto Nacional da Propriedade Industrial do Brasil Re. Application No. BR112018074045-4 and Its Summary of Written Opinion in English. (6 Pages).
Requisition by the Examiner Dated Jun. 9, 2023 From the Innovation, Science and Economic Development Canada, Canadian Intellectual Property Office Re. Application No. 3,024,079. (6 Pages).
Restriction Official Action Dated Aug. 2, 2021 from the US Patent and Trademark Office Re. U.S. Appl. No. 16/885,311. (8 pages).
Restriction Official Action Dated May 3, 2022 from US Patent and Trademark Office Re. U.S. Appl. No. 17/052,834. (6 pages).
Restriction Official Action Dated Oct. 1, 2020 from the US Patent and Trademark Office Re. U.S. Appl. No. 16/304,145. (9 pages).

(56) References Cited

OTHER PUBLICATIONS

Restriction Official Action Dated Jul. 12, 2021 from the US Patent and Trademark Office Re. U.S. Appl. No. 16/884,362. (8 pages).
Restriction Official Action Dated Nov. 15, 2022 from the US Patent and Trademark Office Re. U.S. Appl. No. 17/287,574. (14 pages).
Supplementary European Search Report and the European Search Opinion Dated Aug. 13, 2021 From the European Patent Office Re. Application No. 18883157.2 (120 Pages).
Supplementary European Search Report and the European Search Opinion Dated Aug. 13, 2021 From the European Patent Office Re. Application No. 18883823.9. (8 Pages).
Supplementary European Search Report and the European Search Opinion Dated Oct. 25, 2019 From the European Patent Office Re. Application No. 17802323.0. (9 Pages).
Translation Dated Jan. 13, 2023 of Notification of Office Action Dated Dec. 28, 2022 From the China National Property Administration Re. Application No. 201880086827.5. (3 Pages).
Translation Dated Jul. 14, 2021 of Notification of Office Action Dated Jul. 2, 2021 From the State Intellectual Property Office of the People's Republic of China Re. Application No. 201780037868.0. (6 Pages).
Translation Dated Jun. 17, 2023 of Decision on Rejection Dated May 29, 2023 From the State Intellectual Property Office of the People's Republic of China Re. Application No. 201880086827.5. (3 pages).
Translation Dated Jan. 19, 2023 of Notification of Office Action Dated Jan. 9, 2023 From the State Intellectual Property Office of the People's Republic of China Re. Application No. 201780037868.0. (6 Pages).
Al-Ahmad et al. "Mitigation of Establishment of *Brassica napus* Transgenes in Volunteers Using A Tandem Construct Containing A Selectively Unfit Gene", Plant Biotechnology Journal, XP055444715, 4(1): 7-21, Jan. 2006. Abstract, p. 16, r-h Col. 1st Para, p. 17, 1-h Col. 4th Para.
Al-Ahmad et al. "Mitigation Using A Tandem Construct Containing A Selectively Unfit Gene Precludes Establishment of *Brassica napus* Transgenes in Hybrids and Backcrosses With Weedy *Brassica rapa*", Plant Biotechnology Journal, XP055444720, 4(1): 23-33, Published Online Aug. 16, 2005.
Andreichenko et al. "Possibility of Regulating Seed Formation During Pollination with Mixed Pollen Containing γ-irradiated Pollen", A. A. Bogomolets Kiev Medical Institute, Kiev, Doklady, Biological Sciences, 315(1-6): 699-702, ref.15, Dec. 1990.
Bae et al. "Production of Unbolting Lines Through Gamma-Ray Irradiation Mutagenesis in Genetically Modified Herbicide-Tolerant Zoysia Japonica", Breeding Science, 59(1): 103-105, 2009.
Brewbaker et al. "Pollen Radiobotany", Radiation Botany, 1: 101-154, 1962.
Chin et al. "Pollination With Irradiated Pollen in Rice—*Oryza sativa* L. 1. First (M1) Generation", Heredity, 63(2): 163-170, Published Online Oct. 1, 1989.
Culpepper et al. "Glyphosate-Resistant Palmer Amaranth (*Amaranthus palmeri*) Confirmed in Georgia", Weed Science, 54(4):620-626, Jul. 1, 2006.
Daher et al. "Optimization of Conditions for Germination of Cold-Stored *Arabidopsis thaliana* Pollen", Plant Cell Reports, 28: 347-357, 2009.
Feng et al. "Effect of Enhanced Ultraviolet-B Radiation on Pollen Germination and Tube Growth of 19 Taxa in Vitro", Environmental and Experimental Botany, 43(1):45-53, Feb. 2000.
Germana "Use of Irradiated Pollen to Induce Parthenogenesis and Haploid Production in Fruit Crops", Plant Mutation Breeding and Biotechnology, XP009516584, C30: 411-416, Published Online Dec. 31, 2012.
Gressel et al. "A Strategy to Provide Long-Term Control of Weedy Rice While Mitigating Herbicide Resistance Transgene Flow, and Its Potential Use for Other Crops With Related Weeds", Pest Management Science, XP055053395, 65(7): 723-731, Published Online Apr. 14, 2009.
Hansen "Precision Pollination. Mechanical Pollination Could end Use of Chemicals or Hand Labor for Thinning." Retrieved from The Internet: www.goodfruit.com, 4 pages, Mar. 18, 2015.
He "Garden Plant Breeding", China Forestry Publishing House:174-189, Aug. 1992. Chinese Document only).
Jordan et al. "Biorational Management Tactics to Select Against Triazine-Resistant Amaranthus Hybridus: A Field Trial", Journal of Applied Ecology, 36(1): 123-132, Feb. 1999.
Keller et al. "Genetic Introgression From Distant Provenances Reduces Fitness in Local Weed Populations", Journal of Applied Ecology, 37(4): 647-659, Aug. 2000.
Kosmrlj et al. "Haploid Induction in Hull-less Seed Pumpkin through Parthenogenesis Induced by X-ray-irradiated Pollen". Journal of the American Society for Horticultural Science. 138(4):310-316.(Year:2013).
Kurtar "Influence of Gamma Irradiation on Pollen Viability, Germination Ability, and Fruit and Seed-Set of Pumpkin and Winter Squash", African Journal of Biotechnology, 8(24): 6918-6926, Dec. 15, 2009.
Kwit et al. "Transgene Introgression in Crop Relatives: Molecular Evidence and Mitigation Strategies", Trends in Biotechnology, XP002794936, 29(6): 284-293, Published Online Mar. 8, 2011.
Lagera et al. "Varying Sugars and Sugar Concentrations Influence In Vitro Pollen Germination and Pollen Tube Growth of *Cassia alata* L.", Journal of Young Investigations, 33(1): 42-45, Jun. 2017.
Li et al. "Effects of Sowing Date on Phenotypic Plasticity of Fitness-Related Traits in Two Annual Weeds on the Songnen Plain of China", PLOS ONE, 10(5): e0127795-1-0127795-15, May 29, 2005.
Ma "Why Don't They Genetically Modify Weeds Instead fo Crops? Wouldn't It Make More Sense to Genetically Alter Species of Weeds to Become Interfile After A Few Generations, Thereby Reducing the Need for Herbicides?", Quora.com, 1 P., Apr. 2, 2014.
Marcelis et al. "Flower and Fruit Abortion in Sweet Pepper in Relation to Source and Sink Strength", Journal of Experimental Botany, 55(406): 2261-2268, Oct. 2004.
Munusamy et al. "Female Reproductive System of Amaranthus as the Target for Agrobacterium-Mediated Transformation", Advances in Biscience and Biotechnology, 4(2): 188-192, Published Online Feb. 28, 2013.
Murphy "The Role of Pollen Allelopathy in Weed Ecology", Weed Technology, 15(4):867-872, Dec. 2001.
Muthoni et al. "Reproductive Biology and Early Generation's Selection in Conventional Potato Breeding", Australian Journal of Crop Science, 6(3): 488-497, Mar. 2012.
Peixe et al. "Gamma-Irradiated Pollen Induces the Formation of 2n Endosperm and Abnormal Embryo Development in European Plum (*Prunus domestica* L., Cv. 'Rainha Claudia Verde')", Scientia Horticulturae, 86(4): 267-278, Dec. 2000.
Preston et al. "A Decade of Glyphosate-Resistant Lolium around the World: Mechanisms, Genes, Fitness, and Agronomic Management", Weed Science, 57(4):435-441, Jul. 1, 2009.
Ribeiro et al. "Involvement of Facultative Apomixis in Inheritance of EPSPS Gene Amplification in Glyphosate-resistant Amaranthus Palmeri", Planta, 239: 199-212, 2014.
Shu "Use of Irradiated Pollen to Induce Pathogenesis and Haploid Production in Fruit Crops", Plant Mutation Breeding and Biotechnology, C30: 412-416, Dec. 2012.
Spaunhorst et al. "Phenology of Five Palmer Amaranth (*Amaranthus palmeri*) Populations Grown in Northern Indiana and Arkansas", Weed Science 66(4): 457-469, Mar. 27, 2018.
Tacconi et al. "Kiwifruit Pollination: the Interaction Between Pollen Quality, Pollination Systems and Flowering Stage", Journal of Berry Research, 6(4): 417-426, Dec. 12, 2016.
Yang et al. "Molecular Genetic Analysis of Pollen Irradiation Mutagenesis in *Arabidopsis*", New Phytologist, XP055615348, 164(2): 279-288, Published Online Sep. 10, 2004.
Notice of Allowance Dated Dec. 13, 2023 from the US Patent and Trademark Office Re. U.S. Appl. No. 17/287,574. (17 pages).
Official Action Dated Dec. 7, 2023 from the US Patent and Trademark Office Re. U.S. Appl. No. 16/884,362. (23 pages).
Official Action Dated Dec. 7, 2023 from the US Patent and Trademark Office Re. U.S. Appl. No. 16/885,311. (23 pages).

(56) References Cited

OTHER PUBLICATIONS

Ward et al. "Palmer Amaranth (*Amaranthus palmeri*): A Review", Weed Technology, 27: 12-27, Jan.-Mar. 2013.
Official Action Dated Jun. 6, 2024 from the US Patent and Trademark Office Re. U.S. Appl. No. 16/884,362. (12 pages).
Requisition by the Examiner Dated May 22, 2024 From the Innovation, Science and Economic Development Canada, Canadian Intellectual Property Office Re. Application No. 3,100,078. (3 Pages).

* cited by examiner

METHODS OF CONTROLLING WEED OF THE *AMARANTH* GENUS

RELATED APPLICATION

This application is a division of U.S. patent application Ser. No. 17/052,834, filed on Nov. 4, 2020, which is a National Phase of PCT Patent Application No. PCT/IB2019/053688 having International Filing Date of May 6, 2019, which claims the benefit of priority under 35 USC § 119(e) of U.S. Provisional Patent Application No. 62/667,521 filed on May 6, 2018. The contents of the above applications are all incorporated by reference as if fully set forth herein in their entirety.

FIELD AND BACKGROUND OF THE INVENTION

The present invention, in some embodiments thereof, relates to methods of controlling weed of the amaranth genus.

Weeds have been the major biotic cause of crop yield loses since the origins of agriculture. The potential of weed damages is estimated as 34% loss of crop yield, on average, world-wide [Oerke, E-C., 2006]. In the USA alone, the annual cost of crop losses due to weeds is greater than 26 billion USD [Pimentel D et al., 2000]. Furthermore according to the Weed Science Society of America Weeds are estimated to cause more than 40 billion USD in annual global losses [wssa(dot)net/wssa/weed/biological-control/]. Weeds are thus a major threat to food security [Delye et al., 2013].

Herbicides are the most commonly used and effective weed control tools. Due to the intense selection pressure exerted by herbicides, herbicide resistance is constantly growing and as of 2016 there are over 470 weed biotypes currently identified as being herbicide resistant to one or more herbicides by The International Survey of Herbicide Resistant Weeds (weedscience(dot)org/).

Weeds, like other plants, have several sexual reproduction mechanisms: self-pollination, cross-pollination, or both. Self-pollination describes pollination using pollen from one flower that is transferred to the same or another flower of the same plant. Cross-pollination describes pollination using pollen delivered from a flower of a different plant. Weeds rely on wind, or animals such as bees and other insects to pollinate them.

Since the 1940's the use of sterile organisms has been reported for use in order to reduce pest population and the success of these methods was demonstrated in many cases such as the tsetse fly [Klassen& Curtis, 2005], melon fly [Yosiaki et al. 2003] and Sweet potato weevil [Kohama et al., 2003].

Planting in the field plants producing sterile pollen for the production of infertile seeds was mentioned but immediately over-ruled due to practical, regulatory and economic reasons. (quora(dot)com/Why-dont-they-genetically-modify-weeds-instead-of-crops).

Additional background art includes:

PCT Publication No. WO2017/203519

Korres and Norsworthy (2017), Weed Science, 65(4):491-503.

Keeley et. Al, 1987; *Weed Science* Vol. 35, No. 2 (March, 1987), pp. 199-204.

Clay et al., 2016; Weed Science Society of America, Annual Meeting. San Juan, Puerto Rico, Feb. 8-11, 2016.

Wu and Owen, 2014; Weed Science, 62(1):107-117.

SUMMARY OF THE INVENTION

According to an aspect of some embodiments of the present invention there is provided a method of *Amaranthus* control, the method comprising artificially pollinating an *Amaranthus* species at a growth area with an effective amount of pollen that reduces fitness of the at least one *Amaranthus* species, the effective amount comprising 1 mg to 1 gram per plant per application using a precision tool-assisted application or 10 gram to 100 kg per acre per application using a non-precision tool-assisted application during a flowering season of the *Amaranthus* species.

According to an aspect of some embodiments of the present invention there is provided a method of *Amaranthus* control, the method comprising artificially pollinating an *Amaranthus* species at a growth area with an effective amount of pollen that reduces fitness of the at least one *Amaranthus* species, the effective amount comprising 1-100 applications during a flowering season of the *Amaranthus* species.

According to an aspect of some embodiments of the present invention there is provided a method of *Amaranthus* control, the method comprising artificially pollinating an *Amaranthus* species with an effective amount of pollen that reduces fitness of the at least one *Amaranthus* species, the effective amount comprising repeated applications spanning from daily applications to once every two months during a flowering season of the *Amaranthus* species.

According to some embodiments of the invention, the artificially pollinating is precision tool-assisted.

According to some embodiments of the invention, the artificially pollinating is precision tool-assisted and wherein the effective amount comprises 1-100 applications during a flowering season of the *Amaranthus* species and/or repeated applications spanning from daily applications to once every two months during a flowering season of the *Amaranthus* species.

According to some embodiments of the invention, the artificially pollinating is precision tool-assisted and wherein the effective amount comprises 1 mg to 1 gram per plant per application and/or repeated applications spanning from daily applications to once every two months during a flowering season of the *Amaranthus* species.

According to some embodiments of the invention, the artificially pollinating is precision tool-assisted and wherein the effective amount comprises 1 mg to 1 gram per plant per application and/or comprises 1-100 applications during a flowering season of the *Amaranthus* species.

According to some embodiments of the invention, the effective amount comprises 1-300 mg per plant per application.

According to some embodiments of the invention, the effective amount comprises repeated applications spanning from weekly applications to once every two months during a flowering season of the *Amaranthus* species.

According to some embodiments of the invention, the effective amount comprises repeated applications spanning from two applications a week to once every two months during a flowering season of the *Amaranthus* species According to some embodiments of the invention, the effective amount comprises 1-100 applications during a flowering season of the *Amaranthus* species.

According to some embodiments of the invention, the effective amount comprises 1-10 applications during a flowering season of the *Amaranthus* species.

According to some embodiments of the invention, artificially pollinating is non-precision tool-assisted.

According to some embodiments of the invention, the artificially pollinating is non-precision tool-assisted and wherein the effective amount comprises 1-10 applications during a flowering season of the *Amaranthus* species and/or repeated applications spanning from weekly applications to once every two months during a flowering season of the *Amaranthus* species.

According to some embodiments of the invention, the artificially pollinating is non-precision tool-assisted and wherein the effective amount comprises 1-10 applications during a flowering season of the *Amaranthus* species and/or repeated applications spanning from two applications per week to once every two months during a flowering season of the *Amaranthus* species.

According to some embodiments of the invention, the artificially pollinating is non-precision tool-assisted and wherein the effective amount comprises 1 kg to 10 kg per acre per application and/or repeated applications spanning from weekly applications to once every two months during a flowering season of the *Amaranthus* species.

According to some embodiments of the invention, the artificially pollinating is non-precision tool-assisted and wherein the effective amount comprises 10 g to 100 kg per acre per application and/or repeated applications spanning from two applications per week to once every two months during a flowering season of the *Amaranthus* species.

According to some embodiments of the invention, the artificially pollinating is non-precision tool-assisted and wherein the effective amount comprises 10 g to 100 kg per acre per application and/or comprises 1-10 applications during a flowering season of the *Amaranthus* species.

According to some embodiments of the invention, the pollen and the *Amaranthus* species of interest are of the same species.

According to some embodiments of the invention, the pollen and the *Amaranthus* species of interest are of different species.

According to some embodiments of the invention, the pollen is herbicide resistant.

According to some embodiments of the invention, the pollen is coated with the herbicide.

According to some embodiments of the invention, the *Amaranthus* species of interest is selected from the group consisting of a biotic stress or abiotic stress resistant *Amaranthus.*

According to some embodiments of the invention, the *Amaranthus* species of interest is a herbicide resistant *Amaranthus.*

According to some embodiments of the invention, the pollen is of a herbicide susceptible *Amaranthus.*

According to some embodiments of the invention, the herbicide susceptible *Amaranthus* is susceptible to a plurality of herbicides.

According to some embodiments of the invention, the pollen reduces productiveness of the *Amaranthus* species of interest.

According to some embodiments of the invention, reduction in the productiveness is manifested by:

(i) inability to develop an embryo;

(ii) embryo abortion;

(iii) seed non-viability;

(iv) seed that cannot fully develop; and/or (v) seed that is unable to germinate.

According to some embodiments of the invention, the pollen is non-genetically modified pollen.

According to some embodiments of the invention, the non-genetically modified pollen is produced from a plant having an imbalanced chromosome number.

According to some embodiments of the invention, the pollen is genetically modified pollen.

According to some embodiments of the invention, the *Amaranthus* species of interest is *A. palmeri.*

According to some embodiments of the invention, the *Amaranthus* species of interest is *A. tuberculatus.*

According to some embodiments of the invention, the pollen comprises irradiated pollen.

According to some embodiments of the invention, the pollen comprises X-ray irradiated pollen or gamma-irradiated pollen.

According to some embodiments of the invention, the pollen is a monospecies pollen.

According to some embodiments of the invention, the pollen is a heterospecies pollen.

According to some embodiments of the invention, the heterospecies pollen is of *A. palmeri* and *A. tuberculatus.*

According to some embodiments of the invention, the pollinating is effected prior to, concomitant with or following treatment with a herbicide.

According to some embodiments of the invention, the pollinating is effected prior to and/or post harvesting of the crop and/or at late season.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

DESCRIPTION OF SPECIFIC EMBODIMENTS OF THE INVENTION

The present invention, in some embodiments thereof, relates to methods of controlling weed of the amaranth genus.

Before explaining at least one embodiment of the invention in detail, it is to be understood that the invention is not necessarily limited in its application to the details set forth in the following description or exemplified by the Examples. The invention is capable of other embodiments or of being practiced or carried out in various ways.

Amaranth weed species have an extended period of germination, rapid growth, and high rates of seed production, and have been causing problems for farmers since the mid-1990s. This is partially due to the reduction in tillage, reduction in herbicidal use and the evolution of herbicidal resistance in several species where herbicides have been applied more often. The following 9 species of *Amaranthus* are considered invasive and noxious weeds in the U.S and Canada: *A. albus, A. blitoides, A. hybridus, A. palmeri, A. powellii, A. retroflexus, A. spinosus, A. tuberculatus*, and *A. viridis.*

Herbicide-resistant Amaranth have also been reported e.g., of *Amaranthus palmeri*, and are of grave concern. The species *Amaranthus palmeri* (Palmer amaranth) causes the greatest reduction in soybean yields and has the potential to reduce yields by 17-68% in field experiments. Palmer amaranth is among the "top five most troublesome weeds" in the southeast of the United States and has already evolved resistances to dinitroaniline herbicides and acetolactate synthase inhibitors.

The present inventors have devised a novel method for the biological control of weeds of the Amaranth genus. The approach is based on artificially pollinating the Amaranth weed using an effective amount of pollen to out-compete the native pollen so as to cause reduction in fitness of the weed.

As is illustrated hereinbelow and in the Examples section which follows, the present inventors were able to show that artificial pollination of weed of the Amaranth genus can be effectively achieved by daily applications, every 3 days and once a week. The three regimen tested showed that in all, more than 94% of the seeds that were obtained were aborted seeds (see Example 1). In addition, as shown in Example 2, the average total seed weight did not change significantly between different amounts of pollen per application, namely pollen amount of 120 mg as well as 20 mg per plant in a single application—yielded similar pollination efficiencies.

These results infer on the technical simplicity and cost-affectivity of the methods of some embodiments of the present invention.

Thus, according to an aspect of the invention there is provided a method of *Amaranthus* control, the method comprising artificially pollinating an *Amaranthus* species at a growth area with an effective amount of pollen that reduces fitness of the at least one *Amaranthus* species, the effective amount comprising 1 mg to 1 gram per plant per application using a precision tool-assisted application or 1 kg to 10 kg per acre per application using a non-precision tool-assisted application during a flowering season of the *Amaranthus* species.

According to an aspect of the invention there is provided a method of *Amaranthus* control, the method comprising artificially pollinating an *Amaranthus* species at a growth area with an effective amount of pollen that reduces fitness of the at least one *Amaranthus* species, the effective amount comprising 1-100 applications during a flowering season of the *Amaranthus* species.

According to an aspect of the invention there is provided a method of *Amaranthus* control, the method comprising artificially pollinating an *Amaranthus* species with an effective amount of pollen that reduces fitness of the at least one *Amaranthus* species, the effective amount comprising repeated applications spanning from daily applications to once every two months during a flowering season of the *Amaranthus* species.

As mentioned, embodiments of the invention refer to controlling weed of the *Amaranthus* genus.

The *Amaranthus* genus, collectively known as amaranth, is a cosmopolitan genus of annual or short-lived perennial plants.

According to a specific embodiment, the weed is of the *Amaranthus* selected from the group consisting of:

redroot pigweed (*A. retroflexus*)
smooth pigweed (*A. hybridus*)
Powell amaranth (*A. powelii*)
Palmer amaranth (*A. palmeri*)
spiny amaranth (*A. spinosus*)
tumble pigweed (*A. albus*)
prostrate pigweed (*A. blitoides*)
waterhemp (*A. tuberculatus*=*A. rudis* or *A. rudis* Sauer)

According to a specific embodiment, the pollen is of A. *Palmeri.*

According to a specific embodiment, the pollen is of *A. tuberculatus.*

It will be appreciated that plants of the *Amaranthus* genus can fertilize cross-species. Hence the present teachings relate to mono-species pollen or heterospecies pollen i.e., pollen of two *Amaranthus* species e.g., *A. palmeri* and *A. tuberculatus.*

Any reference done in the present specification to a weed is meant to refer to a weed of the Amaranth genus including all *Amaranthus* species, e.g., *A. palmeri.*

Different weed may have different growth habits and therefore specific weeds usually characterize a certain crop in given growth conditions.

According to a specific embodiment, the weed is a herbicide resistant weed.

According to a specific embodiment, weed is defined as herbicide resistant when it meets the Weed Science Society of America (WSSA) definition of resistance.

Accordingly, WSSA defines herbicide resistance as "the inherited ability of a plant to survive and reproduce following exposure to a dose of herbicide normally lethal to the wild type. Alternatively, herbicide resistance is defined as "The evolved capacity of a previously herbicide-susceptible weed population to withstand a herbicide and complete its life cycle when the herbicide is used at its normal rate in an agricultural situation" (Source: Heap and Lebaron. 2001 in Herbicide Resistance and World Grains).

As used herein the phrase "weed control" refers to suppressing growth and optionally spread of a population of at least one weed species of interest and even reducing the size of the population in a given growth area (predetermined, having clear boundaries).

According to a specific embodiment, the growth area is an urban area, e.g., golf courses, athletic fields, parks, cemeteries, roadsides, home gardens/lawns and the like.

According to an additional or alternative embodiment, the growth area is a rural area.

According to an additional or an alternative embodiment, the growth area is an agricultural growth area e.g., open field, greenhouse, plantation, vineyard, orchard and the like.

According to a specific embodiment, the growth area comprises crop plants (e.g., from seeds to full grown plants and anywhere in-between).

As mentioned, weed control according to the present teachings is effected by reducing fitness of the at least one weed species of interest.

As used herein "fitness" refers to the relative ability of the weed species of interest to develop, reproduce or propagate and transmit its genes to the next generation. As used herein "relative" means in comparison to a weed of the same species not having been artificially pollinated with the pollen of the invention and grown under the same conditions.

It will be appreciated that the effect of pollen treatment according to the present teachings is typically manifested in the first generation after fertilization.

The fitness may be affected by reduction in productiveness, propagation, fertility, fecundity, biomass, biotic stress tolerance, abiotic stress tolerance and/or herbicide resistance.

As used, herein "productivity" refers to the potential rate of incorporation or generation of energy or organic matter by an individual, population or trophic unit per unit time per unit area or volume; rate of carbon fixation.

As used herein "fecundity" refers to the potential reproductive capacity of an organism or population, measured by the number of gametes.

According to a specific embodiment, the pollen affects any stage of seed development or germination.

According to a specific embodiment, the reduction in productiveness is manifested by at least one of:

(i) inability to develop an embryo;

(ii) embryo abortion;

(iii) seed non-viability;

(iv) seed that cannot fully develop; and/or (v) seed that is unable to germinate.

It will be appreciated that when pollen reduces the productiveness, fertility, propagation ability or fecundity of the weed in the next generation it may be referred to by the skilled artisan as sterile pollen, though it fertilizes the weed of interest. Hence, sterile pollen as used herein is still able to fertilize but typically leads to seed developmental arrest or seed abortion.

According to a specific embodiment, the reduction in fitness is by at least 10%, 20%, 30%, 40%, 50%, 60%, 70%, 75%, 80%, 85%, 90%, 92%, 95%, 97% or even 100%, within first generation after fertilization and optionally second generation after fertilization and optionally third generation after fertilization.

According to a specific embodiment, the reduction in fitness is by at least 10%, 20%, 30%, 40%, 50%, 60%, 70%, 75%, 80%, 85%, 90%, 92%, 95%, 97% or even 100%, within first generation after fertilization.

According to a specific embodiment, reduced fitness results from reduction in tolerance to biotic or abiotic conditions e.g., herbicide resistance.

Non-limiting examples of abiotic stress conditions include, salinity, osmotic stress, drought, water deprivation, excess of water (e.g., flood, waterlogging), etiolation, low temperature (e.g., cold stress), high temperature, heavy metal toxicity, anaerobiosis, nutrient deficiency (e.g., nitrogen deficiency or nitrogen limitation), nutrient excess, atmospheric pollution, herbicide, pesticide and UV irradiation.

Biotic stress is stress that occurs as a result of damage done to plants by other living organisms, such as bacteria, viruses, fungi, parasites, beneficial and harmful insects, weeds, and cultivated or native plants.

Examples of herbicides which are contemplated according to the present teachings, include, but are not limited to, ACCase inhibitors, ALS inhibitors, Photosystem II inhibitors, PSII inhibitor (Ureas and amides), PSII inhibitors (Nitriles), PSI Electron Diverter, PPO inhibitors, Carotenoid biosynthesis inhibitors, HPPD inhibitors, Carotenoid biosynthesis (unknown target), EPSP synthase inhibitors, Glutamine synthase inhibitors, DHP synthase inhibitors, Microtubule inhibitors, Mitosis inhibitors, Long chain fatty acid inhibitors, Cellulose inhibitors, Uncouplers, Lipid Inhibitors (thiocarbamates), Synthetic Auxins, Auxin transport inhibitors, Cell elongation inhibitors, Antimicrotubule mitotic disrupter, Nucleic acid inhibitors or any other form of herbicide site of action.

As used herein "pollen" refers to viable pollen that is able to fertilize the weed species of interest and therefore competes with native pollination.

Alternatively, when native pollen competition does not exist, or very low levels of native pollen are present, pollination by the designed pollen inhibits apomixis of weeds and by this reduces their quantities as well [Ribeiro et al. 2012 Abstracts of the Weed Science Society of America Annual Meeting. www(dot)wssaabstracts(dot)com/public/9/abstract-438(dot)html].

According to a specific embodiment, the pollen is of the same species as of the target weed (e.g., invasive, aggressive weed).

According to a specific embodiment, the pollen exhibits susceptibility to a single growth condition e.g., herbicide, temperature.

According to a specific embodiment, the pollen exhibits susceptibility to multiple growth conditions e.g., different herbicides.

According to a specific embodiment, the pollen is non-genetically modified.

The pollen may therefore be of a naturally occurring plant that reduces the fitness of the at least one weed species of interest. According to a specific embodiment, *A. palmeri* or *A. tuberculatus* susceptible seeds are available from the Agriculture Research Service National Plant Germplasm System plant introduction (USDA-ARS_NPGS PI) as well as from various locations in Israel.

Alternatively or additionally, the pollen may be of a plant that has been selected towards producing pollen that reduces the fitness of the at least one weed species of interest.

Selection can be effected by way of exposing the weed to various concentrations of, for example, a herbicide or a plurality of different herbicides, and selecting individuals which show increased susceptibility to the herbicide or different herbicides. Alternatively or additionally, different plants exhibiting susceptibility to different herbicides can be crossed to generate a plant exhibiting susceptibility to a number of herbicides of interest.

It will be appreciated that such breeding need not engage into pedigree breeding programs as the mere product is the pollen of a weedy plant.

Methods of producing pollen that can be used in artificial pollination according to embodiments of the invention are provided below.

According to a specific embodiment, the pollen is irradiated pollen (e.g., X-ray).

As used herein "artificial pollination" is the application, by hand, use of insects (e.g., bees) or dedicated machinery, of fertile stigmas with the pollen.

Artificial pollination in the field can be achieved by pollen spraying (e.g., wet or dry spray formulations), spreading, dispersing or any other method. The application itself will be performed by ground based machinery, aerial based machinery, aircraft, unmanned aerial vehicles (UAV), remote-piloted vehicles (RPV), drones or specialized robots, special vehicles or tractors, insect assisted, specialized apparatus that is designed to spread boosts of pollen, specialized apparatus that combines ventilation and spraying of pollen to enhance recycling of pollen or any other application method or apparatus wherein application can be designed for a single dose, multiple doses, continuous, on an hourly/daily/weekly/monthly basis or any other application timing methodology.

According to a specific embodiment, when using ground machinery, it is preferably adapted not to affect the crop plants at the growth area.

For instance, according to a specific embodiment, crop height is taken into consideration. An illustrative example is provided. Machinery in the field during Palmer Amaranth flowering: During this flowering period (Late July to September, Arkansas, Korres and Norseworthy, 2017) crop height is high. Corn full size can reach at least 1.2 meter, soybean is around 60-80 cm and cotton is around 75-110 cm. This fact dictates the type of tools that can be used.

According to a non-limiting embodiment, the ground equipment that is available for use in fields during this period is the 'High-clearance' tractors that have a high frame structure (50-80 inches height) that allow in-crop spraying without injuring the crop, e.g., High clearance tractors by Hagie and Case IH or such tractors by Miller can be used in-season spraying while crop is high.

These tractors are manufactured by several companies such as Hagie, Case IH and Miller. In addition, such tractors are equipped with a 'boom height control system' that enables automatic control of spraying height above the ground and the crop. These systems optimize spraying positioning and minimize crop injury while spraying.

Conversely, aerial application accounts for almost 20% of all applied crop protection products on commercial farms in the US. According to a USDA Economic Research Service Report, 71 million acres (out of 286 million acres of cropland in the US) is treated aerially every year. While corn and soybean are among the five most commonly treated crops by aerial applicator operators. (www(dot)agaviation (dot)org/industryfacts). Thus, aerial application can be used to determine the weed species/pollinate in the field during the correct time without injuring the crop.

Additional tools that can be used include more advanced tools such as unmanned aerial vehicles (UAV), remote-piloted vehicles (RPV), drones or specialized robots.

Another potential application methodology includes the use of:

1. Insects e.g., honey bees (for pollination);
2. bee vectoring technology (BVT), employing an inoculum dispenser system that is incorporated into the lid of a commercial bee hive. Commercially-reared bees enter the dispenser through a one-way return flap and exit through another portal. As they do so, they pass through and pick up powder material (in this case weed pollen) in BVT's Vectorpak™, taking it with them as they leave the hive (www(dot)beevt(dot)com/about/);
3. robot bee-actually referring to pollination drawns (www(dot)cbinsightsdotcom/research/walmart-farming-drones-patent/?utm_source=CB+Insights+Newsletter&utm_campaign=2edf6b8381-TuesNL_03_20_2018&utm_medium=email&utm_term=0_9dc0513989-2edf6b8381-87383133),
4. robobees (www(dot)wyss(dot)harvard.edu/technology/autonomous-flying-microrobots-robobees/)
5. robo-bee (www(dot)npr(dot)org/sections/thesalt/2017/03/03/517785082/rise-of-the-robot-bees-tiny-drones-turned-into-artificial-pollinators)

In all of these methods, bees or robots/drones mimicking bees display the pollen in either an undirected or directed way onto weed flowering plants or specifically weed flowering female plants in the field.

Each and any of the above tools can be coupled to an agricultural precision tool.

Precision agriculture (PA), satellite farming or site specific crop management (SSCM) is a farming management concept based on observing, measuring and responding to inter and intra-field variability in crops. The goal of precision agriculture research is to define a decision support system (DSS) for whole farm management with the goal of optimizing returns on inputs while preserving resources.

Among these many approaches is a phytogeomorphological approach which ties multi-year crop growth stability/characteristics to topological terrain attributes. The interest in the phytogeomorphological approach stems from the fact that the geomorphology component typically dictates the hydrology of the farm field.

The practice of precision agriculture has been enabled by the advent of GPS and GNSS. The farmer's and/or researcher's ability to locate their precise position in a field allows for the creation of maps of the spatial variability of as many variables as can be measured (e.g. crop yield, terrain features/topography, organic matter content, moisture levels, nitrogen levels, pH, EC, Mg, K, and others). Similar data is collected by sensor arrays mounted on GPS-equipped combine harvesters. These arrays consist of real-time sensors that measure everything from chlorophyll levels to plant water status, along with multispectral imagery. This data is used in conjunction with satellite imagery by variable rate technology (VRT) including seeders, sprayers, etc. to optimally distribute resources.

Precision agriculture has also been enabled by unmanned aerial vehicles like the DJI Phantom which are relatively inexpensive and can be operated by novice pilots. These systems, commonly known as drones, can be equipped with hyperspectral or RGB cameras to capture many images of a field that can be processed using photogrammetric methods to create orthophotos and NDVI maps.

According to a specific embodiment, the use of a technique called multispectral analysis is used. This technique looks at how strongly plants absorb or reflect different wavelengths of sunlight, they can discover which weed species is to be targeted and where.

Sensors attached to moving machinery (ground or aerial) can even take measurements on the run. For example, multispectral sensors mounted on a tractor's spraying booms.

Thus, data can be collected on the go i.e., in real time while treating the crop/weed.

According to a specific embodiment, pollination is precision tool-assisted. i.e., employees a precision tool.

Precision agriculture (PA), satellite farming or site specific crop management (SSCM) is a farming management concept based on observing, measuring and responding to inter and intra-field variability in crops. The goal of precision agriculture research is to define a decision support system (DSS) for whole farm management with the goal of optimizing returns on inputs while preserving resources.

Among these many approaches is a phytogeomorphological approach which ties multi-year crop growth stability/characteristics to topological terrain attributes. The interest in the phytogeomorphological approach stems from the fact that the geomorphology component typically dictates the hydrology of the farm field.

The practice of precision agriculture has been enabled by the advent of GPS and GNSS. The farmer's and/or researcher's ability to locate their precise position in a field allows for the creation of maps of the spatial variability of as many variables as can be measured (e.g. crop yield, terrain features/topography, organic matter content, moisture levels, nitrogen levels, pH, EC, Mg, K, and others). Similar data is collected by sensor arrays mounted on GPS-equipped combine harvesters. These arrays consist of real-time sensors that measure everything from chlorophyll levels to plant water status, along with multispectral imagery. This data is used in conjunction with satellite imagery by variable rate technology (VRT) including seeders, sprayers, etc. to optimally distribute resources.

Precision agriculture has also been enabled by unmanned aerial vehicles like the DJI Phantom which are relatively inexpensive and can be operated by novice pilots. These systems, commonly known as drones, can be equipped with hyperspectral or RGB cameras to capture many images of a field that can be processed using photogrammetric methods to create orthophotos and NDVI maps.

According to embodiments of the invention, a precision tool can be used along with ground-based machinery.

According to embodiments of the invention, a precision tool can be used along with ground-based machinery.

According to a specific embodiment, the precision tool is fuel-operated.

According to a specific embodiment, the precision tool is electrical.

According to a specific embodiment, the precision tool is a device.

According to a specific embodiment, the precision tool is an insect, i.e., pollinating insect such as bees. It will be appreciated that other pollinators can be used however, they first need to be loaded with the pollen of the invention.

As mentioned, the present inventors have realized that weed control of the Amaranth genus can be achieved even at low amounts of pollen per pollination, using limited times of application that can be separated by even months from one application to the other.

The numbers provided herein are per a flowering season.

As used herein "a flowering season" refers to the period in which the first weed plant comprises a receptive stigma until the point that all weed flowers in that area are no longer receptive. It will be appreciated that pollen may be used prior to the appearance of receptive flowering as long as it is viable enough to pollinate upon initiation of stigma receptivity.

Flowers can be unisexual (with either male or female organs) or bisexual (with male stamens and female pistils). Flowering plant species can have separate male and female flowers on the same plant (monoecious) or separate male and female individuals within the population (dioecious).

Stigmas of *A. tuberculatus* var. *rudis* unfertilized female flowers can persist indefinitely until pollen reaches them, consistent with observations on another dioecious species, *A. cannabinus* (Quinn et al. J. Torrey Bot. Soc. 127: 83-86 2000). After fertilization, the stigmas dry out. (Costea et al., Canadian Journal of Plant Science, 2005, 85(2): 507-522).

For instance, synchronized flowering is taken place in *Amaranthus palmeri* (A. *Palmeri*) weed. Korres and Norsworthy (2017) conducted field experiments in Arkansas University during the summers of 2014 and 2015 and they investigated *A. palmeri* flowering initiation and progress. According to their observations *A. palmeri* weed emerges at late June and its flowering initiation starts at the end of July or the beginning of August (about 30-40 days after emergence) and continues for approximately 40-50 days. In addition, it has been demonstrated that the flowering period of *A. palmeri* population is relatively synchronized and it is independent from the plant emergence date as it is regulated by environmental conditions such as day length and temperature (Keeley et. Al, 1987; Korres and Norsworthy, 2017; Clay et al., 2016). Similar observations regarding flowering synchronization were also reported for *A. tuberculatus* (Wu and Owen, 2014).

According to some embodiments, the selected regimen depends on the use of precision tools, the economical burden of the pollination (taking into consideration the pollen price and the pollination machinery operation) and the effect on the crop in the field, which should be as minimized as possible.

Thus, according to a specific embodiment, the effective amount of the pollen comprises 1 mg to 1 gr per plant per application using a precision tool assisted application.

According to a specific embodiment, the effective amount of the pollen comprises 1 mg to 300 mg per plant per application using a precision tool assisted application.

According to a specific embodiment, the effective amount of the pollen comprises 10 mg to 300 mg per plant per application using a precision tool assisted application.

According to a specific embodiment, the effective amount of the pollen comprises 50 mg to 300 mg per plant per application using a precision tool assisted application.

According to a specific embodiment, the effective amount of the pollen comprises 100 mg to 300 mg per plant per application using a precision tool assisted application.

According to a specific embodiment, the effective amount of the pollen comprises 150 mg to 300 mg per plant per application using a precision tool assisted application.

According to a specific embodiment, the effective amount of the pollen comprises 1 mg to 3 mg per plant per application using a precision tool assisted application.

According to a specific embodiment, the effective amount of the pollen comprises 1 mg to 5 mg per plant per application using a precision tool assisted application.

According to a specific embodiment, the effective amount of the pollen comprises 1 mg to 10 mg per plant per application using a precision tool assisted application.

According to a specific embodiment, the effective amount of the pollen comprises 1 mg to 20 mg per plant per application using a precision tool assisted application.

According to a specific embodiment, the effective amount of the pollen comprises 1 mg to 50 mg per plant per application using a precision tool assisted application.

According to a specific embodiment, the effective amount of the pollen comprises 20 mg to 100 mg per plant per application using a precision tool assisted application.

The ranges of 1-10 mg per plant per application are especially preferred when using insects as pollinators such as bees.

According to a specific embodiment, the effective amount of the pollen comprises 10 gr to 100 kg per acre per application using a non-precision tool assisted application.

According to a specific embodiment, the effective amount of the pollen comprises 10 gr to 90 kg per acre per application using a non-precision tool assisted application.

According to a specific embodiment, the effective amount of the pollen comprises 10 gr to 80 kg per acre per application using a non-precision tool assisted application.

According to a specific embodiment, the effective amount of the pollen comprises 10 gr to 70 kg per acre per application using a non-precision tool assisted application.

According to a specific embodiment, the effective amount of the pollen comprises 10 gr to 60 kg per acre per application using a non-precision tool assisted application.

According to a specific embodiment, the effective amount of the pollen comprises 10 gr to 50 kg per acre per application using a non-precision tool assisted application.

According to a specific embodiment, the effective amount of the pollen comprises 10 gr to 40 kg per acre per application using a non-precision tool assisted application.

According to a specific embodiment, the effective amount of the pollen comprises 10 gr to 30 kg per acre per application using a non-precision tool assisted application.

According to a specific embodiment, the effective amount of the pollen comprises 10 gr to 20 kg per acre per application using a non-precision tool assisted application.

According to a specific embodiment, the effective amount of the pollen comprises 10 gr to 10 kg per acre per application using a non-precision tool assisted application.

According to a specific embodiment, the effective amount of the pollen comprises 10 gr to 5 kg per acre per application using a non-precision tool assisted application.

According to a specific embodiment, the effective amount of the pollen comprises 10 gr to 1 kg per acre per application using a non-precision tool assisted application.

According to a specific embodiment, the effective amount of the pollen comprises 10 gr to 0.1 kg per acre per application using a non-precision tool assisted application.

According to a specific embodiment, the effective amount of the pollen comprises 10 gr to 1000 gr per acre per application using a non-precision tool assisted application.

According to a specific embodiment, the effective amount of the pollen comprises 10 gr to 800 gr per acre per application using a non-precision tool assisted application.

According to a specific embodiment, the effective amount of the pollen comprises 10 gr to 700 gr per acre per application using a non-precision tool assisted application.

According to a specific embodiment, the effective amount of the pollen comprises 10 gr to 600 gr per acre per application using a non-precision tool assisted application.

According to a specific embodiment, the effective amount of the pollen comprises 10 gr to 500 gr per acre per application using a non-precision tool assisted application.

According to a specific embodiment, the effective amount of the pollen comprises 10 gr to 400 gr per acre per application using a non-precision tool assisted application.

According to a specific embodiment, the effective amount of the pollen comprises 10 gr to 300 gr per acre per application using a non-precision tool assisted application.

According to a specific embodiment, the effective amount of the pollen comprises 10 gr to 200 gr per acre per application using a non-precision tool assisted application.

According to a specific embodiment, the effective amount of the pollen comprises 1 kg to 10 kg per acre per application using a non-precision tool assisted application.

According to a specific embodiment, the effective amount of the pollen comprises 1 kg to 7 kg per acre per application using a non-precision tool assisted application.

According to a specific embodiment, the effective amount of the pollen comprises 1 kg to 6 kg per acre per application using a non-precision tool assisted application.

According to a specific embodiment, the effective amount of the pollen comprises 1 kg to 5 kg per acre per application using a non-precision tool assisted application.

According to a specific embodiment, the effective amount of the pollen comprises 1 kg to 4 kg per acre per application using a non-precision tool assisted application.

According to a specific embodiment, the effective amount of the pollen comprises 1 kg to 3 kg per acre per application using a non-precision tool assisted application.

According to a specific embodiment, the effective amount of the pollen comprises 1 kg to 2 kg per acre per application using a non-precision tool assisted application.

According to a specific embodiment, the effective amount of the pollen comprises 1-100 applications during a flowering season of the weed.

According to a specific embodiment, the effective amount of the pollen comprises 10-100 applications during a flowering season of the weed.

According to a specific embodiment, the effective amount of the pollen comprises 20-100 applications during a flowering season of the weed.

According to a specific embodiment, the effective amount of the pollen comprises 30-100 applications during a flowering season of the weed.

According to a specific embodiment, the effective amount of the pollen comprises 40-100 applications during a flowering season of the weed.

According to a specific embodiment, the effective amount of the pollen comprises 50-100 applications during a flowering season of the weed.

According to a specific embodiment, the effective amount of the pollen comprises 60-100 applications during a flowering season of the weed.

According to a specific embodiment, the effective amount of the pollen comprises 70-100 applications during a flowering season of the weed.

According to a specific embodiment, the effective amount of the pollen comprises 80-100 applications during a flowering season of the weed.

According to a specific embodiment, the effective amount of the pollen comprises 1-80 applications during a flowering season of the weed.

According to a specific embodiment, the effective amount of the pollen comprises 1-50 applications during a flowering season of the weed.

According to a specific embodiment, the effective amount of the pollen comprises 1-30 applications during a flowering season of the weed.

According to a specific embodiment, the effective amount of the pollen comprises 1-15 applications during a flowering season of the weed.

According to a specific embodiment, the effective amount of the pollen comprises 1-10 applications during a flowering season of the weed.

According to a specific embodiment, the effective amount of the pollen comprises 3-50 applications during a flowering season of the weed.

According to a specific embodiment, the effective amount of the pollen comprises 3-20 applications during a flowering season of the weed.

According to a specific embodiment, the effective amount of the pollen comprises 5-15 applications during a flowering season of the weed (e.g., using unmanned aerial vehicles such as drones or by insect pollinators such as using bees).

According to a specific embodiment, the effective amount of the pollen comprises 6-15 applications during a flowering season of the weed (e.g., using unmanned aerial vehicles such as drones or by insect pollinators such as using bees).

According to a specific embodiment, the effective amount of the pollen comprises 7-15 applications during a flowering season of the weed (e.g., using unmanned aerial vehicles such as drones or by insect pollinators such as using bees).

According to a specific embodiment, the effective amount of the pollen comprises 8-15 applications during a flowering season of the weed (e.g., using unmanned aerial vehicles such as drones or by insect pollinators such as using bees).

According to a specific embodiment, the effective amount of the pollen comprises 9-15 applications during a flowering season of the weed (e.g., using unmanned aerial vehicles such as drones or by insect pollinators such as using bees).

According to a specific embodiment, the effective amount of the pollen comprises 10-15 applications during a flowering season of the weed (e.g., using unmanned aerial vehicles such as drones or by insect pollinators such as using bees).

According to a specific embodiment, the effective amount of the pollen comprises 5-10 applications during a flowering season of the weed (e.g., using unmanned aerial vehicles such as drones or by insect pollinators such as using bees).

According to a specific embodiment, the effective amount of the pollen comprises 7-10 applications during a flowering season of the weed (e.g., using unmanned aerial vehicles such as drones or by insect pollinators such as using bees).

According to a specific embodiment, the effective amount of the pollen comprises daily applications during a flowering season of the weed (e.g., using unmanned aerial vehicles such as drones or by insect pollinators such as using bees).

According to a specific embodiment, the effective amount of the pollen comprises weekly applications during a flowering season of the weed (e.g., using unmanned aerial vehicles such as drones or by insect pollinators such as using bees).

According to a specific embodiment, the effective amount of the pollen comprises 1-4 applications during a flowering season of the weed (e.g., using ground machinery or aerial machinery).

According to a specific embodiment, the effective amount of the pollen comprises 1-3 applications during a flowering season of the weed (e.g., using ground machinery or aerial machinery).

According to a specific embodiment, the effective amount of the pollen comprises 1-2 applications during a flowering season of the weed (e.g., using ground machinery or aerial machinery).

According to a specific embodiment, the effective amount of the pollen comprises 2-4 applications during a flowering season of the weed (e.g., using ground machinery or aerial machinery).

According to a specific embodiment, the effective amount of the pollen comprises 3-4 applications during a flowering season of the weed (e.g., using ground machinery or aerial machinery).

As mentioned, dependent on the operability and/or effectivity of the pollinators or pollinating machinery and/or the effect on crop, the applications may be spaced having selected intervals in between pollinations during a flowering season.

According to a specific embodiment, the effective amount comprises repeated applications 1 per day (daily) to 1 per 2 months during the flowering season of the weed.

According to a specific embodiment, the effective amount comprises repeated applications 1 per day to 1 per 7 weeks during the flowering season of the weed.

According to a specific embodiment, the effective amount comprises repeated applications 1 per day to 1 per 6 weeks during the flowering season of the weed.

According to a specific embodiment, the effective amount comprises repeated applications 1 per day to 1 per 4 weeks during the flowering season of the weed.

According to a specific embodiment, the effective amount comprises repeated applications 1 per day to 1 per 3 weeks during the flowering season of the weed.

According to a specific embodiment, the effective amount comprises repeated applications 1 per day to 1 per 2 weeks during the flowering season of the weed.

According to a specific embodiment, the effective amount comprises repeated applications 1 per day to 1 per 1 week during the flowering season of the weed.

It will be appreciated that any of the above regimen can be combined e.g., number of applications 5-15 from using 1 mg to 300 mg pollen per plant, daily.

Thus, according to an embodiment, the artificially pollinating is precision tool-assisted.

According to a specific embodiment, the artificially pollinating is precision tool-assisted and the effective amount comprising 1 mg to 1 gram per plant per application using a precision tool-assisted application or 1 kg to 10 kg per acre per application using a non-precision tool-assisted application during a flowering season of the *Amaranthus* species and wherein the effective amount comprises 1-100 applications during a flowering season of the *Amaranthus* species and/or repeated applications spanning from daily applications to once every two months during a flowering season of the *Amaranthus* species.

According to a specific embodiment, the artificially pollinating is precision tool-assisted the effective amount comprising 1-100 applications during a flowering season of the *Amaranthus* species and wherein the effective amount comprises 1 mg to 1 gram per plant per application and/or repeated applications spanning from daily applications to once every two months during a flowering season of the *Amaranthus* species.

According to a specific embodiment, the artificially pollinating is precision tool-assisted and wherein the effective amount comprises 1 mg to 1 gram per plant per application and/or comprises 1-100 applications during a flowering season of the *Amaranthus* species.

According to a specific embodiment, the effective amount comprises 1-300 mg per plant per application.

According to a specific embodiment, the effective amount comprising 1 mg to 1 gram per plant per application using a precision tool-assisted application or 10 g to 100 kg per acre per application using a non-precision tool-assisted application during a flowering season of the *Amaranthus* species and/or the effective amount comprising 1-100 applications during a flowering season of the *Amaranthus* species and the effective amount comprises repeated applications spanning from weekly applications to once every two months during a flowering season of the *Amaranthus* species According to a specific embodiment, the effective amount comprising 1 mg to 1 gram per plant per application using a precision tool-assisted application or 10 g to 100 kg per acre per application using a non-precision tool-assisted application during a flowering season of the *Amaranthus* species and wherein the effective amount comprises 1-100 applications during a flowering season of the *Amaranthus* species.

According to a specific embodiment, the artificially pollinating is non-precision tool-assisted, the effective amount comprising 1 mg to 1 gram per plant per application using a precision tool-assisted application or 10 g to 100 kg per acre per application using a non-precision tool-assisted application during a flowering season of the *Amaranthus* species and wherein the effective amount comprises 1-10 applications during a flowering season of the *Amaranthus* species and/or repeated applications spanning from weekly applications to once every two months during a flowering season of the *Amaranthus* species.

According to a specific embodiment, the artificially pollinating is non-precision tool-assisted, the effective amount comprising 1-100 applications during a flowering season of the *Amaranthus* species and wherein the effective amount comprises 10 g to 100 kg per acre per application and/or repeated applications spanning from weekly applications to once every two months during a flowering season of the *Amaranthus* species.

According to a specific embodiment, the effective amount comprising repeated applications spanning from daily applications to once every two months during a flowering season of the *Amaranthus* species and wherein the artificially pollinating is non-precision tool-assisted and wherein the effective amount comprises 10 g to 100 kg per acre per application and/or comprises 1-10 applications during a flowering season of the *Amaranthus* species.

According to a specific embodiment, the effective amount comprising 1 mg to 1 gram per plant per application using a precision tool-assisted application or 1 kg to 10 kg per acre per application using a non-precision tool-assisted application during a flowering season of the *Amaranthus* species and/or the effective amount comprising 1-100 applications during a flowering season of the *Amaranthus* species and the effective amount comprises repeated applications spanning from weekly applications to once every two months during a flowering season of the *Amaranthus* species According to a specific embodiment, the effective amount comprising 1 mg to 1 gram per plant per application using a precision tool-assisted application or 1 kg to 10 kg per acre per application using a non-precision tool-assisted application during a flowering season of the *Amaranthus* species and wherein the effective amount comprises 1-100 applications during a flowering season of the *Amaranthus* species.

According to a specific embodiment, the artificially pollinating is non-precision tool-assisted, the effective amount comprising 1 mg to 1 gram per plant per application using a precision tool-assisted application or 1 kg to 10 kg per acre per application using a non-precision tool-assisted application during a flowering season of the *Amaranthus* species and wherein the effective amount comprises 1-10 applications during a flowering season of the *Amaranthus* species and/or repeated applications spanning from weekly applications to once every two months during a flowering season of the *Amaranthus* species.

According to a specific embodiment, the artificially pollinating is non-precision tool-assisted, the effective amount comprising 1-100 applications during a flowering season of the *Amaranthus* species and wherein the effective amount comprises 1 kg to 10 kg per acre per application and/or repeated applications spanning from weekly applications to once every two months during a flowering season of the *Amaranthus* species.

According to a specific embodiment, the effective amount comprising repeated applications spanning from daily applications to once every two months during a flowering season of the *Amaranthus* species and wherein the artificially pollinating is non-precision tool-assisted and wherein the effective amount comprises 1 kg to 10 kg per acre per application and/or comprises 1-10 applications during a flowering season of the *Amaranthus* species.

According to a specific embodiment, the effective amount comprises repeated applications spanning from two applications a week to once every two months during a flowering season of said *Amaranthus* species According to a specific embodiment, the artificially pollinating is non-precision tool-assisted and wherein said effective amount comprises 1-10 applications during a flowering season of said *Amaranthus* species and/or repeated applications spanning from two applications per week to once every two months during a flowering season of said *Amaranthus* species.

According to a specific embodiment, the artificially pollinating is non-precision tool-assisted and wherein said effective amount comprises 10 g to 100 kg per acre per application and/or repeated applications spanning from two applications per week to once every two months during a flowering season of said *Amaranthus* species.

According to a specific embodiment, the application can be continuous throughout the flowering season such as by using a static puffer.

Tables 1 and 2 below list some embodiments of the invention, which separates between the use of precision tools or without them.

TABLE 1

| | Precision tools | | Non-precision tools | |
|---|---|---|---|---|
| | Possibility for high number of applications during flowering season (such as drones or robotic bees) | Few applications during flowering season (such as High clearance tractors-Hagie tractors or other brands or drones on fuel) | Ground equipment such as tractors | Air equipment - aircrafts |
| Number of applications | 1-100 | 1-10 | 1-10 | 1-10 |
| Interval between applications | From 1 day to 2 months | From twice a week to once every 2 months | From twice a week to once every 2 months | From twice a week to once every 2 months |
| Amount of pollen per weed plant (or female weed plant for dioicous species) per application | 1 mg-1 g | 1 mg-1 gr | NA | NA |
| Amount of pollen per acre per application | NA | NA | 10 g-100 kg | 0.1 kg-100 kg |

TABLE 2

| | Precision tools | | Non-precision tools | |
|---|---|---|---|---|
| | Possibility for high number of applications during flowering season (such as drones or robotic bees) | Few applications during flowering season (such as High clearance tractors-Hagie tractors or other brands or drones on fuel) | Ground equipment such as tractors | Air equipment - aircrafts |
| Number of applications | 3-50 and 5-15 e.g., for drones or Natural bees - every day | 1-4 | 1-4 | 1-4 |

TABLE 2-continued

| | Precision tools | | Non-precision tools | |
|---|---|---|---|---|
| | Possibility for high number of applications during flowering season (such as drones or robotic bees) | Few applications during flowering season (such as High clearance tractors-Hagie tractors or other brands or drones on fuel) | Ground equipment such as tractors | Air equipment - aircrafts |
| Amount of pollen per weed plant (or female weed plant for dioicous species) per application | 1 mg-0.3 g For natural bees it can be even lower amounts per bee (but in that case it may be calculated on hive level) | 1 mg-0.3 gr | NA | NA |
| Amount of pollen per acre per application | NA | NA | 10 g-10 kg | 0.1 kg-10 kg |

According to another specific embodiment, only female flowers are pollinated while male flowers are either left untreated or treated using other means, e.g., herbicides, harvesting etc.

It will be appreciated that at any time the weed of interest can be further treated with other weed control means as a part of an integrated weed management program. For example, the weed may be treated with a herbicide (which is usually applied at early stages of germination as opposed to the pollen, which is applied at flowering). For instance, pollination can be effected post crop emergence and prior to and/or post harvesting of said crop and/or at late season. For instance, in the weeds *Amaranthus palmeri* and *Amaranthus tuberculatus* interfering in a corn, soybean or cotton field pollination can be applied during late season. Thus a herbicide for instance can be applied prior to, concomitantly with or following pollen treatment.

Any of the pollen compositions described herein can be produced as a single species pollen with a single trait for reducing weed fitness, a single species pollen with a plurality of traits for reducing weed fitness (e.g., a number of different herbicide resistances or a number of sterility encoding mechanisms) all introduced into a single weed or to a plurality of weeds of the same species, a multispecies pollen with a single trait or a multispecies pollen with a plurality of said traits.

According to a specific embodiment, there is provided a method of producing pollen that reduces fitness of at least one weed species of interest, the method comprising treating the weed species of interest (e.g., seeds, seedlings, tissue/cells) or pollen thereof with an agent that reduces fitness.

When needed (such as when treating that weed (e.g., seeds, seedlings, tissue/cells) the method further comprises growing or regenerating the plant so as to produce pollen.

According to a specific embodiment, the method comprises harvesting pollen from the weed species of interest following treating with the agent that reduces the fitness.

It will be appreciated that the pollen may be first harvested and then treated with the agent (e.g., radiation) that reduces the fitness of the weed species of interest.

Alternatively or additionally, the pollen is produced from a plant having an imbalanced chromosome number (genetic load) with the weed species of interest.

Thus, for example, when the weed of interest is diploid, the plant producing the pollen is treated with an agent rendering it polyploid, typically, tetraploids are selected, such that upon fertilization with the diploid female plant an aborted or developmentally arrested, not viable seed set are created. Alternatively, a genomically imbalanced plant is produced which rarely produces a seed set.

According to a specific embodiment, the weed (or a regenerating part thereof or the pollen) is subjected to a polyploidization protocol using a polyploidy inducing agent, that produces plants, which are able to cross but result in reduced productiveness, Thus, according to some embodiments of the invention, the polyploid weed has a higher chromosome number than the wild type weed species (e.g., at least one chromosome set or portions thereof) such as for example two folds greater amount of genetic material (i.e., chromosomes) as compared to the wild type weed. Induction of polyploidy is typically performed by subjecting a weed tissue (e.g., seed) to a G2/M cycle inhibitor.

Typically, the G2/M cycle inhibitor comprises a microtubule polymerization inhibitor.

Examples of microtubule cycle inhibitors include, but are not limited to oryzalin, colchicine, colcemid, trifluralin, benzimidazole carbamates (e.g. nocodazole, oncodazole, mebendazole, R 17934, MBC), o-isopropyl N-phenyl carbamate, chloroisopropyl N-phenyl carbamate, amiprophos-methyl, taxol, vinblastine, griseofulvin, caffeine, bis-ANS, maytansine, vinbalstine, vinblastine sulphate and podophyllotoxin.

According to a specific embodiment, the microtubule cycle inhibitor is colchicine.

Still alternatively or additionally, the weed may be selected producing pollen that reduces fitness of the weed species of interest by way of subjecting it to a mutagenizing agent and if needed further steps of breeding.

Thus, weed can be exposed to a mutagen or stress followed by selection for the desired phenotype (e.g., pollen sterility, herbicide susceptibility).

Examples of stress conditions which can be used according to some embodiments of the invention include, but are not limited to, X-ray radiation, gamma radiation, particle irradiation such as alpha, beta or other accelerated particle, UV radiation or alkylating agents such as NEU, EMS, NMU and the like. The skilled artisan will know which agent to select.

According to a specific embodiment, the stress is selected from the group consisting of X-ray radiation, gamma radiation, UV radiation. For example, pollen of the weed can be treated with the agent that reduces the fitness (e.g., radiation) following harvest.

Guidelines for plant mutagenesis are provided in K Lindsey Plant Tissue Culture Manual—Supplement 7: Fundamentals and Applications, 1991, which is hereby incorporated in its entirety.

Other mutagenizing agents include, but are not limited to, alpha radiation, beta radiation, neutron rays, heating, nucleases, free radicals such as but not limited to hydrogen peroxide, cross linking agents, alkylating agents, BOAA, DES, DMS, EI, ENH, MNH, NMH Nitrous acid, bisulfate, base analogs, hydroxyl amine, 2-Naphthylamine or alfatoxins.

Alternatively or additionally, the pollen may be genetically modified pollen (e.g., transgenic pollen, DNA-editing).

Numerous methods are known for exploiting genetic modification to render it suitable for reducing the fitness of a weed species of interest.

Thus, according to a specific embodiment, the pollen is genetically modified pollen.

According to other specific embodiments, the trait being inherited upon artificial pollination with the pollen of the invention is selected from the group consisting of embryo abortion, seed non-viability, seeds with structural defects, seeds that are unable to germinate, abiotic/biotic stress susceptibility (e.g., herbicide susceptibility) or induced death or sensitivity upon chemical or physical induction or any other inherited property that will enable controlled reduction of weed population size.

Often sterile pollen results in a seedless plant. A plant is considered seedless if it is not able to produce seeds, traces of aborted seeds or a much-reduced number of seeds. In other cases the pollen will produce plants with seeds that are unable to germinate or develop e.g., no embryo or embryo abortion.

According to a specific embodiment, the pollen is genetically modified to express an exogenous transgene that upon fertilization will reduce fitness of the weed of interest (next generation). Such a gene is termed a "disrupter gene". According to some embodiments, the disrupter gene causes kills the weed species of interest, accordingly it is termed a "death gene".

According to a specific embodiment, the pollen is genetically modified to express a silencing agent that upon fertilization will reduce fitness of the weed of interest (next generation).

According to a specific embodiment, the pollen is genetically modified to express a genome editing agent that upon fertilization will reduce fitness of the weed of interest (next generation).

In some embodiments of the invention, the genetic modification is effected in an inducible manner to minimize the effect on the weed producing the pollen product of the invention (i.e., that reduces the fitness of the plant of interest).

Genetic Use Restriction Technology (GURT).

Embodiments of the invention make use of this technology which provides specific genetic switch mechanisms that hamper reproduction (variety specific V-GURT) or the expression of a trait (trait-specific T-GURT) in a genetically modified (transgenic) plant.

Variety GURT (also known as suicide/sterile seed/gene technology or terminator technology) is designed to control plant fertility or seed development through a genetic process triggered by a chemical inducer that will allow the plant to grow and to form seeds, but will cause the embryo of each of those seeds to produce a cell toxin that will prevent its germination if replanted, thus causing second generation seeds that will not germinate.

T-GURT (ironically known as traitor technology) is designed to switch on or off a trait (such as herbicide/cold/drought/stress tolerance, pest resistance, germination, flowering or defense mechanisms) using inducible promoters regulating the expression of the transgene through induced gene silencing (e.g., by antisense suppression) or by excision of the transgene using a recombinase. In this case, the genetic modification is activated by a chemical treatment or by physical factors e.g., environmental factors such as heat.

These methods are reviewed by Lombardo 2014 Plant Biotechnology Journal 12:995-1005, U.S. Pat. No. 5,364,780, WO9403619, WO9404393, U.S. Pat. No. 5,723,765 each of which is incorporated herein by reference.

Both methods can rely on site-specific recombination of DNA in plant cells. Typically the recombination system employed is from bacteriophage P1. The system comprises a recombinase (Cre) and recombination sites (loxP). In the presence of Cre, recombination between loc sites occurs on supercoiled, nicked, circular or linear DNA. Alternative recombination systems are: Flp/frt, R/RS, Gin/Gix. Specific signal sequences can be selected from the group comprising LOX sequences and sequences recognizable by either flippase, resolvase, FLP, SSV1-encoded integrase, or transposase and the second gene that encodes a specific recombinase can be selected from the group comprising CRE, flippase, resolvase, FLP, SSV1-encoded integrase, and transposase.

The activation of a cytotoxic gene using this system is a well known way of producing sterile plants.

For V-GURTs, essentially three different restriction mechanisms are proposed (Visser et al., 2001 Biotechnol. Dev. Monit. 48, 9-12). The first mechanism of action is that described in the patent (U.S. Pat. No. 5,723,765) by the USDA and Delta & Pine Land (nominally the first V-GURT). This GURT is based on the transfer of a combination of three genes (transgenes), two derived from bacteria and one from another plant, into a plant's cells:

1. A gene coding for a cytotoxic protein (the terminator or lethal gene) e.g., under control of a late embryogenesis abundant (LEA) promoter linked to a DNA spacer (blocking) sequence flanked by specific excision sites (lox sequence) that prevents the activation of the terminator gene. In the '765 patent, the cytotoxic protein is the ribosome inactivating protein (RIP), otherwise known as saporin derived from *Saponaria officinalis*, which prevents plant cells from synthesizing proteins. Barnase is an alternative for RIP, as will be further described hereinbelow;
2. A site-specific recombinase gene under the control of a constitutively active promoter (e.g., CaMV 35S) containing one or more tet operons that is subject to repression by the Tet repressor. This gene encodes a recombinase (e.g., Cre) that cuts the specific excision sites flanking the blocking sequence linked to the toxic gene;
3. A repressor gene (e.g., Tn10 tet) under the control of a constitutive promoter and encoding a protein that binds to the responsive operon (e.g., tet), preventing the expression of the recombinase gene. The presence of an external stimulus (chemical or physical inducer) prevents binding of the repressor to the operon. The external stimulus can be chemical inducers such as agrochemicals and antibiotics or physical such as temperature.

In another embodiment of the method, which is also contemplated herein, the recombinase gene is directly linked to an inducible promoter (U.S. Pat. No. 5,723,765).

Potential inducers include, but are not limited to, ethanol, hormones, steroids, (e.g., dexamethasone, glucocorticoid, estrogen, estradiol), salicylic acid, pesticides and metals such as copper, antibiotics such as but not limited to tetracycline, Ecdysone, ACEI, Benzothiadiazole and Safener, Tebufenozide or Methoxyfenozide [Reviewed in Padidam et al., 2003].

It will be appreciated that in sharp contrast to prior art methods, the genetically modified pollen is that of the weed and not that of the crop.

U.S. Pat. No. 5,925,808 describes embodiments of the Genetic Use Restriction Technology, and is hereby incorporated by reference in its entirety.

Following is a non-limiting example, for the use of GURT in conferring weeds with reduced fitness.

Thus, the following constructs can be produced.

1. A gene which expression results in an altered plant phenotype e.g., disrupter gene, linked to a transiently active promoter, the gene and promoter being separated by a blocking sequence flanked on either side by specific excision sequences.
2. A second gene that encodes a recombinase specific for the specific excision sequences linked to a repressible promoter.
3. A third gene that encodes the repressor specific for the repressible promoter.

Plasmid sequences and procedures can be used as described in U.S. Pat. No. 5,925,808, supra:

According to an exemplary embodiment, the death gene used is RIP (ribosomal inhibitor protein, sequence of a complete RIP gene, saporin 6: GenBank ID SOSAP6, Accession No. X15655) or barnase (Genbank Accession M14442). The CRE Gene is under the control of a Tetracycline-derepressible 35S Promoter. The third plasmid comprises a Tet Repressor Gene Driven by a 35S Promoter.

The transiently active promoter in the first plasmid is expressed during embryogenesis, seed development or seed germination. Optional gene promoters include promoters of embryogenesis genes such as late embryogenesis abundant genes LEA1, LEA2, LEA3, LEA4, LEA5, DEHYDRIN and SMP (Pedrosa et al., 2015), promoters of seed development genes such as LEAFY COTYLEDON genes, including, but not limited to, LEC1, LEC2 and *FUSCA*3 (FUS3), or ABSCISIC ACID INSENSITIVE 3 (ABI3) (Santos-Mendoza et al., 2008). Additional promoters of seed development genes can be taken from multiple comprehensive studies that identified a long list of related genes (see Le et al., 2010 and McElver J et al., 2001). Promoters of Germination genes include but are not limited to Expansin (Chen and Bradford., 2000), endo-β-mannase (Nonogaki H et al., 2000), β-1,3-glucanase (Leubner-Metzger and Meins, 2000 and Wu et al., 2001), extension like protein ERP1 (Dubreucq et al., 2000) as well as genes that are related to abscisic acid (ABA) and gibberellic acid (GA) biosynthesis (Shu et al., 2015 and Toorop et al., 2000).

Other construct systems which can be used rely on a transcriptional inducible system. In such constructs, transcription is reversibly turned on or off in the presence of an analyte e.g., antibiotic e.g., tetracycline or one of its derivatives (e.g. doxycycline). Such are described in Wikipedia and is summarized infra. Briefly, the Tet-Off system makes use of the tetracycline transactivator (tTA) protein, which is created by fusing one protein, TetR (tetracycline repressor), found in *Escherichia coli* bacteria, with the activation domain of another protein, VP16, found in the Herpes Simplex Virus.

The resulting tTA protein is able to bind to DNA at specific TetO operator sequences. In most Tet-Off systems, several repeats of such TetO sequences are positioned upstream of a minimal promoter. The entirety of several TetO sequences with a minimal promoter is called a tetracycline response element (TRE), because it responds to binding of the tetracycline transactivator protein (tTA) by increased expression of the gene or genes downstream of its promoter. In a Tet-Off system, expression of TRE-controlled genes can be repressed by tetracycline and its derivatives (e.g., doxycycline, anhydrotetracycline). They bind tTA and render it incapable of binding to TRE sequences, thereby preventing transactivation of TRE-controlled genes. A Tet-On system works similarly, but in the opposite fashion. While in a Tet-Off system, tTA is capable of binding the operator only if not bound to tetracycline or one of its derivatives, such as doxycycline, in a Tet-On system, the reverse tetracycline transactivator (rtTA) protein is capable of binding the operator only if bound by a tetracycline. Thus, the introduction of doxycycline to the system initiates the transcription of the genetic product.

Examples for use of these systems include but not limited to the following set of constructs that relies on the Tet ON system:

1. A gene which expression results in an altered plant phenotype linked to a transiently active promoter, the gene and promoter being separated by a blocking sequence flanked on either side by specific excision sequences.
2. A second gene that encodes a recombinase specific for the specific excision sequences linked to an operator that is upstream to the promoter and is responsive to an activator.
3. A third gene that encodes the activator specific for the operator in the second plasmid under a constitutive promoter.

Applied inducer binds the activator protein eliciting a conformational change to its active form.

According to an exemplary embodiment, the death gene used under the control of an embryogenesis, seed development or seed germination promoter is RIP (ribosomal inhibitor protein, sequence of a complete RIP gene, saporin 6:GenBank ID SOSAP6, Accession No. X15655) or barnase (Genbank Accession M14442). The CRE Gene is under the control of a Tet-ON TRE and the third plasmid is a constitutive promoter upstream of an rtTA. Upon application of tetracycline or its derivatives such as doxycycline the rtTA becomes activated and results in expression of the CRE recombinase and consequently activates the death gene.

Another optional set of plasmids that can be used is a simplified two plasmids system that again relies on the Tet-ON system:

1. A gene which expression results in an altered plant phenotype linked to a transiently active promoter and an operator that is upstream to the promoter and is responsive to an activator.
2. A second gene that encodes the activator specific for the operator from the first plasmid under a constitutive promoter.

According to an exemplary embodiment, the death gene used is RIP (ribosomal inhibitor protein, sequence of a complete RIP gene, saporin 6:GenBank ID SOSAP6, Accession No. X15655) or barnase (Genbank Accession M14442). The death gene is under the dual control of both a promoter that is active during embryogenesis, seed development or seed germination as well as a Tet-ON TRE.

And the second plasmid is a constitutive promoter upstream of an rtTA. Upon application of tetracycline or its derivatives such as doxycycline the rtTA becomes activated and results in activation of the death gene.

Yet alternatively or additionally, plants which produce pollen capable of reducing fitness of a weed species of interest can be generated by a hybrid GURT method whereby a dual complementary male and female plant genetic recombination systems are used.

A weed sterile line is being produced by crossing between two homozygous transformed plants. The male and female plants are each transformed with a plasmid encoding a disrupter gene controlled by a transiently active promoter, the gene and promoter being separated by a blocking sequence flanked on either side by specific excision sequences (such as lox or frt excision sequences). In addition the plasmid contains a second gene that encodes a genetic recombination enzyme (such as cre recombinase or flp flippase) specific for the excision sequences in the opposite sex (namely, the recombination enzyme of the female plant cut the excision sequence in the male and vice versa). These recombination enzymes are under the control of a promoter that is active post seed germination stage. The transformed plasmid both in the male and in the female homozygous lines are inserted to the same genomic locus position.

The following plasmid is transformed into the female plant:

Plasmid encoding a barnase or RIP gene under the control of a specific embryogenesis, seed development or germination promoter whereas the gene and promoter being separated by a blocking sequence flanked on either side by specific excision lox sequences and a second gene encoding for a flippase recombination enzyme under a promoter that is active post seed germination.

The following plasmid is transformed into the male plant:

Plasmid encoding a barnase or RIP gene under the control of a specific embryogenesis, seed development or germination promoter whereas the gene and promoter are being separated by a blocking sequence flanked on either side by specific excision frt sequences and a second gene encoding for a cre recombinase recombination enzyme under a promoter that is active post seed germination.

Lines are being selected such that both insertions to both male and female are on the exact same genomic position.

Only upon crossing between these male plants with these female plants both recombination events by flp and cre are occurring thus yielding pollen that have a barnase or RIP gene under the control of a specific embryogenesis, seed development or germination promoter.

Another embodiment of V-GURT contemplated herein (see U.S. Pat. No. 5,808,034, herein incorporated in its entirety) is based on a reversed process because it is characterized by the presence of a gene encoding a disrupter protein that is active in embryogensis seed development or seed germination thus resulting in loss of productiveness. Only upon exposure to a chemical or physical inducer that result in inhibition of the disrupter gene the plant is capable of reproducing normally. It will be appreciated that in sharp contrast to prior art methods, the genetically modified pollen contains the disrupter gene under the regulation of a transiently active promoter that is expressed during embryogenesis, seed development or seed germination and not male flower specific promoters.

Thus, a sterile line can be produced using two plasmids:

1. Plasmid encoding for a disrupter protein under a promoter that is active in the embryo or seed, which makes it sterile where the gene promoter is under the control of a specific operator sequence responsive to repression by a repressor protein.
2. A repressor protein, whose gene is under the control of a constitutive promoter. When binding to a specific chemical the repressor can bind the operator from the first plasmid and inhibit the expression of the disrupter protein. According to an exemplary embodiment, the disrupter gene used under the control of an embryogenesis, seed development or seed germination promoter as well as the control of at least one TetO element is RIP (ribosomal inhibitor protein, sequence of a complete RIP gene, saporin 6: GenBank ID SOSAP6, Accession No. X15655) or barnase (Genbank Accession M14442). The reverse TetR gene (mutated form of the original TetR) is under a constitutive promoter. Upon application of tetracycline or its derivatives such as doxycycline the reverse TetR becomes activated and results in inhibition of expression of the disrupter induced gene.

Alternatively, it can be produced by using the Tet-Off system with the following two plasmids:

1. Plasmid encoding for a disrupter protein under a promoter that is active in the embryo or seed, which makes the plant sterile where the gene promoter is under the control of a specific operator sequence responsive to activation by an activator protein.
2. An activator protein, whose gene is under the control of a constitutive promoter. Upon specific chemical binding to this activator, it becomes non-active and can no longer activate the transcription of the first plasmid.

According to an exemplary embodiment, the disrupter gene used under the control of an upstream TRE followed by an embryogenesis, seed development or seed germination promoter is RIP (ribosomal inhibitor protein, sequence of a complete RIP gene, saporin 6: GenBank ID SOSAP6, Accession No. X15655) or barnase (Genbank Accession M14442). The tTA Gene is under a constitutive promoter. Upon application of tetracycline or its derivatives such as doxycycline the tTA becomes inactivated and results in inhibition of expression of the disrupter induced gene.

It will be appreciated that in the reverse process, the disrupter gene is active however upon application of an inducer; the disrupter gene is turned off allowing the plant to survive and reproduce.

Thus, as mentioned, the disrupter gene promoter is under the control of a specific operator sequence. A further repressor protein, which gene is under control of a chemically or physically inducible promoter, can bind to the operator, inhibiting the expression of the disrupter protein. In the absence of the exogenous chemical inducer, no repressor protein is expressed; therefore, the breeder must apply the specific chemical inducer throughout the process of seed multiplication to inactivate the disrupter gene that causes sterility, terminating the application only at the time of selling the seeds.

A further technology contemplated herein refers to the recoverable block of function (RBF), which consists of a blocking sequence (e.g., encoding a barnase) linked to the gene of interest and a recovery sequence (e.g., encoding a barstar), expressed under control of sulfhydryl endopeptidase (SH-EP) and heat shock (HS) promoters, respectively, and all contained in a single insert. The natural expression of the barnase in embryos and sprouts confers cell death or prevents sexual reproduction (by blocking mRNA synthesis and germination) in the natural environment. The expression of the recovery sequence is induced by an artificial external stimulus such as a heat shock treatment or chemical application; recovery of the blocked function results in the 'restoration' of the viable/fertile phenotype.

Any seed formed from hybridization between wild weed and the GM pollen that contain the RBF will be unable to germinate because of the action of the blocking sequence. It will be appreciated that in sharp contrast to prior art methods, the genetically modified pollen with the RBF system that is used in the artificial pollination and is aimed at weed control does not have a gene of interest coupled to it. Alternatively, or additionally the plant can be transformed with any gene that results in reduced fitness (destruction gene) which expression can be induced.

Various inducible systems are known in the art. These include, but are not limited to, AlcR based ethanol inducible system, Tetracycline system, steroid-inducible systems such as but not limited to Glucocorticoid receptor-based, Dexamethasone-inducible, Estradiol inducible or Estrogen receptor-based, insecticide inducible systems such as but not limited to Ecdysone receptor-based, or ACEI-based, copper-inducible system. Additional inducible systems are Benzothiadiazole-inducible and Safener-inducible, Tebufenozide inducible or, Methoxyfenozide inducible systems [Padidam et al., 2003].

In the same manner the following constructs can be prepared, provided they are under an inducible regulation. Thus, transgenic weeds expressing EtoH inducible death gene are being produced using insertion of a plasmid encoding for AlcR based EtoH inducible promoter linked to a barnase gene or a RIP gene or transgenic plants expressing EtOH inducible EPSPS anti sense RNA to reduce EPSPS levels upon ethanol application.

Examples of genes that can be modulated in order to reduce tolerance to biotic or abiotic stress include, but are not limited to, HSF, MYB, MYC, AP2/ERF, NAC, ZF, HSP, MAPK, LEA, SOS or CYP (Atkinson N J and Urwin P E, 2012); or microRNA families such as MIR156, MIR166, MIR167, MIR169 (Khraiwesh, B. et al., 2012).

Another option is generating a weed strain that produces pollen that is genetically modified to express an inhibitor of a gene that is responsible for herbicide resistance or tolerance (e.g., biotic or abiotic) such as a silencing agent or DNA editing agent (e.g., CRISPR-Cas9, as further detailed below) that modulates expression of a target molecule e.g., herbicide targeted molecule such as but not limited to genes related to ACCase, ALS, Photosystem II, PSI Electron Diverter, PPO, Carotenoid biosynthesis, HPPD, EPSP synthase, Glutamine synthase, DHP synthase, Mitosis, Auxin transport, Uncouplers, Antimicrotubule mitotic disrupter, Cell elongation or in the process of generation of Microtubule, Long chain fatty acid, Cellulose, Lipid, Nucleic acid or modulating expression of any other critical gene participating in the fertilization process, embryonic development, seed development or germination process.

Examples of platform technologies that can be used to down-regulate gene expression include, but are not limited to downregulation (gene silencing) of the transcription or translation product of an endogenous gene can be achieved by co-suppression, antisense suppression, RNA intereference and ribozyme molecules.

Co-suppression (sense suppression)—Inhibition of the endogenous gene can be achieved by co-suppression, using an RNA molecule (or an expression vector encoding same) which is in the sense orientation with respect to the transcription direction of the endogenous gene. The polynucleotide used for co-suppression may correspond to all or part of the sequence encoding the endogenous polypeptide and/or to all or part of the 5' and/or 3' untranslated region of the endogenous transcript; it may also be an unpolyadenylated RNA; an RNA which lacks a 5' cap structure; or an RNA which contains an unsplicable intron.

In some embodiments, the polynucleotide used for co-suppression is designed to eliminate the start codon of the endogenous polynucleotide so that no protein product will be translated. Methods of co-suppression using a full-length cDNA sequence as well as a partial cDNA sequence are known in the art (see, for example, U.S. Pat. No. 5,231,020).

According to some embodiments of the invention, down-regulation of the endogenous gene is performed using an amplicon expression vector, which comprises a plant virus-derived sequence that contains all or part of the target gene but generally not all of the genes of the native virus. The viral sequences present in the transcription product of the expression vector allow the transcription product to direct its own replication. The transcripts produced by the amplicon may be either sense or antisense relative to the target sequence [see for example, Angell and Baulcombe, (1997) *EMBO J.* 16:3675-3684; Angell and Baulcombe, (1999) *Plant J.* 20:357-362, and U.S. Pat. No. 6,646,805, each of which is herein incorporated by reference].

Antisense suppression—Antisense suppression can be performed using an antisense polynucleotide or an expression vector which is designed to express an RNA molecule complementary to all or part of the messenger RNA (mRNA) encoding the endogenous polypeptide and/or to all or part of the 5' and/or 3' untranslated region of the endogenous gene. Over expression of the antisense RNA molecule can result in reduced expression of the native (endogenous) gene. The antisense polynucleotide may be fully complementary to the target sequence (i.e., 100% identical to the complement of the target sequence) or partially complementary to the target sequence (i.e., less than 100% identical, e.g., less than 90%, less than 80% identical to the complement of the target sequence).

Antisense suppression may be used to inhibit the expression of multiple proteins in the same plant (see e.g., U.S. Pat. No. 5,942,657). In addition, portions of the antisense nucleotides may be used to disrupt the expression of the target gene. Generally, sequences of at least about 50 nucleotides, at least about 100 nucleotides, at least about 200 nucleotides, at least about 300, at least about 400, at least about 450, at least about 500, at least about 550, or greater may be used. Methods of using antisense suppression to inhibit the expression of endogenous genes in plants are described, for example, in Liu, et al., (2002) Plant Physiol. 129:1732-1743 and U.S. Pat. Nos. 5,759,829 and 5,942,657, each of which is herein incorporated by reference.

Efficiency of antisense suppression may be increased by including a poly-dT region in the expression cassette at a position 3' to the antisense sequence and 5' of the polyadenylation signal [See, U.S. Patent Publication No. 20020048814, herein incorporated by reference].

RNA intereference—RNA intereference can be achieved using a polynucleotide, which can anneal to itself and form a double stranded RNA having a stem-loop structure (also called hairpin structure), or using two polynucleotides, which form a double stranded RNA.

For hairpin RNA (hpRNA) interference, the expression vector is designed to express an RNA molecule that hybridizes to itself to form a hairpin structure that comprises a single-stranded loop region and a base-paired stem.

In some embodiments of the invention, the base-paired stem region of the hpRNA molecule determines the specificity of the RNA interference. In this configuration, the sense sequence of the base-paired stem region may correspond to all or part of the endogenous mRNA to be down-regulated, or to a portion of a promoter sequence controlling expression of the endogenous gene to be inhibited; and the antisense sequence of the base-paired stem region is fully or partially complementary to the sense sequence. Such hpRNA molecules are highly efficient at inhibiting the expression of endogenous genes, in a manner which is inherited by subsequent generations of plants [See, e.g., Chuang and Meyerowitz, (2000) Proc. Natl. Acad. Sci. USA 97:4985-4990; Stoutjesdijk, et al., (2002) Plant Physiol. 129:1723-1731; and Waterhouse and Helliwell, (2003) Nat. Rev. Genet. 4:29-38; Chuang and Meyerowitz, (2000) Proc. Natl. Acad. Sci. USA 97:4985-4990; Pandolfini et al., BMC Biotechnology 3:7; Panstruga, et al., (2003) Mol. Biol. Rep. 30:135-140; and U.S. Patent Publication No. 2003/0175965; each of which is incorporated by reference].

According to some embodiments of the invention, the sense sequence of the base-paired stem is from about 10 nucleotides to about 2,500 nucleotides in length, e.g., from about 10 nucleotides to about 500 nucleotides, e.g., from about 15 nucleotides to about 300 nucleotides, e.g., from about 20 nucleotides to about 100 nucleotides, e.g., or from about 25 nucleotides to about 100 nucleotides.

According to some embodiments of the invention, the antisense sequence of the base-paired stem may have a length that is shorter, the same as, or longer than the length of the corresponding sense sequence.

According to some embodiments of the invention, the loop portion of the hpRNA can be from about 10 nucleotides to about 500 nucleotides in length, for example from about 15 nucleotides to about 100 nucleotides, from about 20 nucleotides to about 300 nucleotides or from about 25 nucleotides to about 400 nucleotides in length.

According to some embodiments of the invention, the loop portion of the hpRNA can include an intron (ihpRNA), which is capable of being spliced in the host cell. The use of an intron minimizes the size of the loop in the hairpin RNA molecule following splicing and thus increases efficiency of the interference [See, for example, Smith, et al., (2000) Nature 407:319-320; Wesley, et al., (2001) Plant J. 27:581-590; Wang and Waterhouse, (2001) Curr. Opin. Plant Biol. 5:146-150; Helliwell and Waterhouse, (2003) Methods 30:289-295; Brummell, et al. (2003) Plant J. 33:793-800; and U.S. Patent Publication No. 2003/0180945; WO 98/53083; WO 99/32619; WO 98/36083; WO 99/53050; US 20040214330; US 20030180945; U.S. Pat. Nos. 5,034,323; 6,452,067; 6,777,588; 6,573,099 and 6,326,527; each of which is herein incorporated by reference].

In some embodiments of the invention, the loop region of the hairpin RNA determines the specificity of the RNA interference to its target endogenous RNA. In this configuration, the loop sequence corresponds to all or part of the endogenous messenger RNA of the target gene. See, for example, WO 02/00904; Mette, et al., (2000) EMBO J 19:5194-5201; Matzke, et al., (2001) Curr. Opin. Genet. Devel. 11:221-227; Scheid, et al., (2002) Proc. Natl. Acad. Sci., USA 99:13659-13662; Aufsaftz, et al., (2002) Proc. Nat'l. Acad. Sci. 99(4):16499-16506; Sijen, et al., Curr. Biol. (2001) 11:436-440), each of which is incorporated herein by reference.

For double-stranded RNA (dsRNA) interference, the sense and antisense RNA molecules can be expressed in the same cell from a single expression vector (which comprises sequences of both strands) or from two expression vectors (each comprising the sequence of one of the strands). Methods for using dsRNA interference to inhibit the expression of endogenous plant genes are described in Waterhouse, et al., (1998) Proc. Natl. Acad. Sci. USA 95:13959-13964; and WO 99/49029, WO 99/53050, WO 99/61631, and WO 00/49035; each of which is herein incorporated by reference.

According to some embodiments of the invention, RNA intereference is effected using an expression vector designed to express an RNA molecule that is modeled on an endogenous micro RNAs (miRNA) gene. Micro RNAs (miRNAs) are regulatory agents consisting of about 22 ribonucleotides and highly efficient at inhibiting the expression of endogenous genes [Javier, et al., (2003) Nature 425:257-263]. The miRNA gene encodes an RNA that forms a hairpin structure containing a 22-nucleotide sequence that is complementary to the endogenous target gene.

Ribozyme—Catalytic RNA molecules, ribozymes, are designed to cleave particular mRNA transcripts, thus preventing expression of their encoded polypeptides. Ribozymes cleave mRNA at site-specific recognition sequences. For example, "hammerhead ribozymes" (see, for example, U.S. Pat. No. 5,254,678) cleave mRNAs at locations dictated by flanking regions that form complementary base pairs with the target mRNA. The sole requirement is that the target RNA contains a 5'-UG-3' nucleotide sequence. Hammerhead ribozyme sequences can be embedded in a stable RNA such as a transfer RNA (tRNA) to increase cleavage efficiency in vivo [Perriman et al. (1995) Proc. Natl. Acad. Sci. USA, 92(13):6175-6179; de Feyter and Gaudron Methods in Molecular Biology, Vol. 74, Chapter 43, "Expressing Ribozymes in Plants", Edited by Turner, P. C, Humana Press Inc., Totowa, N.J.; U.S. Pat. No. 6,423,885]. RNA endoribonucleases such as that found in *Tetrahymena thermophila* are also useful ribozymes (U.S. Pat. No. 4,987,071).

Constructs useful in the methods according to some embodiments of the invention may be constructed using recombinant DNA technology well known to persons skilled in the art. The gene constructs may be inserted into vectors, which may be commercially available, suitable for transforming into plants and suitable for expression of the gene of interest in the transformed cells. The genetic construct can be an expression vector wherein the nucleic acid sequence is operably linked to one or more regulatory sequences allowing expression in the plant cells.

In a particular embodiment of some embodiments of the invention the regulatory sequence is a plant-expressible promoter.

As used herein the phrase "plant-expressible" refers to a promoter sequence, including any additional regulatory elements added thereto or contained therein, is at least capable of inducing, conferring, activating or enhancing expression in a plant cell, tissue or organ, preferably a monocotyledonous or dicotyledonous plant cell, tissue, or organ. Examples of promoters useful for the methods of some embodiments of the invention are presented in Table 1.

TABLE 3

Exemplary constitutive promoters for use in the performance of some embodiments of the invention

| Gene Source | Expression Pattern | Reference |
|---|---|---|
| Actin | constitutive | McElroy etal, Plant Cell, 2: 163-171, 1990 |
| CAMV 35S | constitutive | Odell et al, Nature, 313: 810-812, 1985 |

TABLE 3-continued

| Exemplary constitutive promoters for use in the performance of some embodiments of the invention | | |
|---|---|---|
| Gene Source | Expression Pattern | Reference |
| CaMV 19S | constitutive | Nilsson et al., Physiol. Plant 100: 456-462, 1997 |
| GOS2 | constitutive | de Pater et al, Plant J Nov; 2(6): 837-44, 1992 |
| ubiquitin | constitutive | Christensen et al, Plant Mol. Biol. 18: 675-689, 1992 |

According to some embodiments of the invention, over-expression is achieved by means of genome editing. However, the same means can be used to down-regulate gene expression all dependent on the design of the gene editing tool.

Genome editing is a reverse genetics method, which uses artificially engineered nucleases to cut and create specific double-stranded breaks at a desired location(s) in the genome, which are then repaired by cellular endogenous processes such as, homology directed repair (HDR) and non-homologous end-joining (NHEJ). NHEJ directly joins the DNA ends in a double-stranded break, while HDR utilizes a homologous sequence as a template for regenerating the missing DNA sequence at the break point. In order to introduce specific nucleotide modifications to the genomic DNA, a DNA repair template containing the desired sequence must be present during HDR. Genome editing cannot be performed using traditional restriction endonucleases since most restriction enzymes recognize a few base pairs on the DNA as their target and the probability is very high that the recognized base pair combination will be found in many locations across the genome resulting in multiple cuts not limited to a desired location.

To overcome this challenge and create site-specific single- or double-stranded breaks, several distinct classes of nucleases have been discovered and bioengineered to date. These include the meganucleases, Zinc finger nucleases (ZFNs), transcription-activator like effector nucleases (TALENs) and CRISPR/Cas system.

Over expression of a polypeptide by genome editing can be achieved by: (i) replacing an endogenous sequence encoding the polypeptide of interest, and/or (ii) inserting a new gene encoding the polypeptide of interest in a targeted region of the genome, and/or (iii) introducing point mutations which result in up-regulation of the gene encoding the polypeptide of interest (e.g., by altering the regulatory sequences such as promoter, enhancers, 5'-UTR and/or 3'-UTR). Downregulation of a gene of interest can be achieved by introducing point mutations which result in down-regulation of the gene encoding the polypeptide of interest (e.g., by altering the regulatory sequences such as promoter, enhancers, 5'-UTR and/or 3'-UTR, inserting mutations in a catalytic site or protein-protein interaction interface).

Homology Directed Repair (HDR).

Homology Directed Repair (HDR) can be used to generate specific nucleotide changes (also known as gene "edits") ranging from a single nucleotide change to large insertions. In order to utilize HDR for gene editing, a DNA "repair template" containing the desired sequence must be delivered into the cell type of interest with the guide RNA [gRNA(s)] and Cas9 or Cas9 nickase. The repair template must contain the desired edit as well as additional homologous sequence immediately upstream and downstream of the target (termed left and right homology arms). The length and binding position of each homology arm is dependent on the size of the change being introduced. The repair template can be a single stranded oligonucleotide, double-stranded oligonucleotide, or double-stranded DNA plasmid depending on the specific application. It is worth noting that the repair template must lack the Protospacer Adjacent Motif (PAM) sequence that is present in the genomic DNA, otherwise the repair template becomes a suitable target for Cas9 cleavage. For example, the PAM could be mutated such that it is no longer present, but the coding region of the gene is not affected (i.e. a silent mutation).

The efficiency of HDR is generally low (<10% of modified alleles) even in cells that express Cas9, gRNA and an exogenous repair template.

For this reason, many laboratories are attempting to artificially enhance HDR by synchronizing the cells within the cell cycle stage when HDR is most active, or by chemically or genetically inhibiting genes involved in Non-Homologous End Joining (NHEJ). The low efficiency of HDR has several important practical implications. First, since the efficiency of Cas9 cleavage is relatively high and the efficiency of HDR is relatively low, a portion of the Cas9-induced double strand breaks (DSBs) will be repaired via NHEJ. In other words, the resulting population of cells will contain some combination of wild-type alleles, NHEJ-repaired alleles, and/or the desired HDR-edited allele.

Therefore, it is important to confirm the presence of the desired edit experimentally, and if necessary, isolate clones containing the desired edit.

The HDR method was successfully used for targeting a specific modification in a coding sequence of a gene in plants (Budhagatapalli Nagaveni et al. 2015. "Targeted Modification of Gene Function Exploiting Homology-Directed Repair of TALEN-Mediated Double-Strand Breaks in Barley". G3 (Bethesda). 2015 September; 5(9): 1857-1863). Thus, the gfp-specific transcription activator-like effector nucleases were used along with a repair template that, via HDR, facilitates conversion of gfp into yfp, which is associated with a single amino acid exchange in the gene product. The resulting yellow-fluorescent protein accumulation along with sequencing confirmed the success of the genomic editing.

Similarly, Zhao Yongping et al. 2016 (An alternative strategy for targeted gene replacement in plants using a dual-sgRNA/Cas9 design. Scientific Reports 6, Article number: 23890 (2016)) describe co-transformation of *Arabidopsis* plants with a combinatory dual-sgRNA/Cas9 vector that successfully deleted miRNA gene regions (MIR169a and MIR827a) and second construct that contains sites homologous to *Arabidopsis* TERMINAL FLOWER 1 (TFL1) for homology-directed repair (HDR) with regions corresponding to the two sgRNAs on the modified construct to provide both targeted deletion and donor repair for targeted gene replacement by HDR.

Activation of Target Genes Using CRISPR/Cas9.

Many bacteria and archaea contain endogenous RNA-based adaptive immune systems that can degrade nucleic acids of invading phages and plasmids. These systems consist of clustered regularly interspaced short palindromic repeat (CRISPR) genes that produce RNA components and CRISPR associated (Cas) genes that encode protein components.

The CRISPR RNAs (crRNAs) contain short stretches of homology to specific viruses and plasmids and act as guides to direct Cas nucleases to degrade the complementary nucleic acids of the corresponding pathogen. Studies of the type II CRISPR/Cas system of *Streptococcus pyogenes* have shown that three components form an RNA/protein complex and together are sufficient for sequence-specific nuclease activity: the Cas9 nuclease, a crRNA containing 20 base pairs of homology to the target sequence, and a trans-activating crRNA (tracrRNA) (Jinek et al. *Science* (2012) 337: 816-821.). It was further demonstrated that a synthetic chimeric guide RNA (gRNA) composed of a fusion between crRNA and tracrRNA could direct Cas9 to cleave DNA targets that are complementary to the crRNA in vitro. It was also demonstrated that transient expression of CRISPR-associated endonuclease (Cas9) in conjunction with synthetic gRNAs can be used to produce targeted double-stranded brakes in a variety of different species.

The CRISPR/Cas9 system is a remarkably flexible tool for genome manipulation. A unique feature of Cas9 is its ability to bind target DNA independently of its ability to cleave target DNA. Specifically, both RuvC- and HNH-nuclease domains can be rendered inactive by point mutations (D10A and H840A in SpCas9), resulting in a nuclease dead Cas9 (dCas9) molecule that cannot cleave target DNA. The dCas9 molecule retains the ability to bind to target DNA based on the gRNA targeting sequence. The dCas9 can be tagged with transcriptional activators, and targeting these dCas9 fusion proteins to the promoter region results in robust transcription activation of downstream target genes. The simplest dCas9-based activators consist of dCas9 fused directly to a single transcriptional activator.

Importantly, unlike the genome modifications induced by Cas9 or Cas9 nickase, dCas9-mediated gene activation is reversible, since it does not permanently modify the genomic DNA.

Indeed, genome editing was successfully used to over-express a protein of interest in a plant by, for example, mutating a regulatory sequence, such as a promoter to overexpress the endogenous polynucleotide operably linked to the regulatory sequence. For example, U.S. Patent Application Publication No. 20160102316 to Rubio Munoz, Vicente et al. which is fully incorporated herein by reference, describes plants with increased expression of an endogenous DDA1 plant nucleic acid sequence wherein the endogenous DDA1 promoter carries a mutation introduced by mutagenesis or genome editing which results in increased expression of the DDA1 gene, using for example, CRISPR. The method involves targeting of Cas9 to the specific genomic locus, in this case DDA1, via a 20 nucleotide guide sequence of the single-guide RNA. An online CRISPR Design Tool can identify suitable target sites (www(dot)tools(dot)genome-engineering(dot)org. Ran et al. Genome engineering using the CRISPR-Cas9 system nature protocols, VOL. 8 NO. 11, 2281-2308, 2013).

The CRISPR-Cas system was used for altering gene expression in plants as described in U.S. Patent Application publication No. 20150067922 to Yang; Yinong et al., which is fully incorporated herein by reference. Thus, the engineered, non-naturally occurring gene editing system comprises two regulatory elements, wherein the first regulatory element (a) operable in a plant cell operably linked to at least one nucleotide sequence encoding a CRISPR-Cas system guide RNA (gRNA) that hybridizes with the target sequence in the plant, and a second regulatory element (b) operable in a plant cell operably linked to a nucleotide sequence encoding a Type-II CRISPR-associated nuclease, wherein components (a) and (b) are located on same or different vectors of the system, whereby the guide RNA targets the target sequence and the CRISPR-associated nuclease cleaves the DNA molecule, thus altering the expression of a gene product in a plant. It should be noted that the CRISPR-associated nuclease and the guide RNA do not naturally occur together.

In addition, as described above, point mutations which activate a gene-of-interest and/or which result in over-expression of a polypeptide-of-interest can be also introduced into plants by means of genome editing. Such mutation can be for example, deletions of repressor sequences, which result in activation of the gene-of-interest; and/or mutations, which insert nucleotides and result in activation of regulatory sequences such as promoters and/or enhancers.

Meganucleases—Meganucleases are commonly grouped into four families: the LAGLIDADG family, the GIY-YIG family, the His-Cys box family and the HNH family. These families are characterized by structural motifs, which affect catalytic activity and recognition sequence. For instance, members of the LAGLIDADG family are characterized by having either one or two copies of the conserved LAGLIDADG motif. The four families of meganucleases are widely separated from one another with respect to conserved structural elements and, consequently, DNA recognition sequence specificity and catalytic activity.

Meganucleases are found commonly in microbial species and have the unique property of having very long recognition sequences (>14 bp) thus making them naturally very specific for cutting at a desired location. This can be exploited to make site-specific double-stranded breaks in genome editing. One of skill in the art can use these naturally occurring meganucleases, however the number of such naturally occurring meganucleases is limited. To overcome this challenge, mutagenesis and high throughput screening methods have been used to create meganuclease variants that recognize unique sequences. For example, various meganucleases have been fused to create hybrid enzymes that recognize a new sequence. Alternatively, DNA interacting amino acids of the meganuclease can be altered to design sequence specific meganucleases (see e.g., U.S. Pat. No. 8,021,867). Meganucleases can be designed using the methods described in e.g., Certo, M T et al. Nature Methods (2012) 9:073-975; U.S. Pat. Nos. 8,304,222; 8,021,867; 8,119,381; 8,124,369; 8,129,134; 8,133,697; 8,143,015; 8,143,016; 8,148,098; or 8,163,514, the contents of each are incorporated herein by reference in their entirety. Alternatively, meganucleases with site specific cutting characteristics can be obtained using commercially available technologies e.g., Precision Biosciences' Directed Nuclease Editor™ genome editing technology.

ZFNs and TALENs—Two distinct classes of engineered nucleases, zinc-finger nucleases (ZFNs) and transcription activator-like effector nucleases (TALENs), have both proven to be effective at producing targeted double-stranded breaks (Christian et al., 2010; Kim et al., 1996; Li et al., 2011; Mahfouz et al., 2011; Miller et al., 2010).

Basically, ZFNs and TALENs restriction endonuclease technology utilizes a non-specific DNA cutting enzyme which is linked to a specific DNA binding domain (either a series of zinc finger domains or TALE repeats, respectively). Typically a restriction enzyme whose DNA recognition site and cleaving site are separate from each other is selected. The cleaving portion is separated and then linked to a DNA binding domain, thereby yielding an endonuclease with very high specificity for a desired sequence. An exemplary restriction enzyme with such properties is Fokl.

Additionally Fokl has the advantage of requiring dimerization to have nuclease activity and this means the specificity increases dramatically as each nuclease partner recognizes a unique DNA sequence.

To enhance this effect, FokI nucleases have been engineered that can only function as heterodimers and have increased catalytic activity. The heterodimer functioning nucleases avoid the possibility of unwanted homodimer activity and thus increase specificity of the double-stranded break.

Thus, for example to target a specific site, ZFNs and TALENs are constructed as nuclease pairs, with each member of the pair designed to bind adjacent sequences at the targeted site. Upon transient expression in cells, the nucleases bind to their target sites and the FokI domains heterodimerize to create a double-stranded break.

Repair of these double-stranded breaks through the non-homologous end-joining (NHEJ) pathway most often results in small deletions or small sequence insertions. Since each repair made by NHEJ is unique, the use of a single nuclease pair can produce an allelic series with a range of different deletions at the target site.

The deletions typically range anywhere from a few base pairs to a few hundred base pairs in length, but larger deletions have successfully been generated in cell culture by using two pairs of nucleases simultaneously (Carlson et al., 2012; Lee et al., 2010).

In addition, when a fragment of DNA with homology to the targeted region is introduced in conjunction with the nuclease pair, the double-stranded break can be repaired via homology directed repair to generate specific modifications (Li et al., 2011; Miller et al., 2010; Urnov et al., 2005).

Although the nuclease portions of both ZFNs and TALENs have similar properties, the difference between these engineered nucleases is in their DNA recognition peptide. ZFNs rely on Cys2-His2 zinc fingers and TALENs on TALEs.

Both of these DNA recognizing peptide domains have the characteristic that they are naturally found in combinations in their proteins. Cys2-His2 Zinc fingers typically found in repeats that are 3 bp apart and are found in diverse combinations in a variety of nucleic acid interacting proteins. TALEs on the other hand are found in repeats with a one-to-one recognition ratio between the amino acids and the recognized nucleotide pairs. Because both zinc fingers and TALEs happen in repeated patterns, different combinations can be tried to create a wide variety of sequence specificities. Approaches for making site-specific zinc finger endonucleases include, e.g., modular assembly (where Zinc fingers correlated with a triplet sequence are attached in a row to cover the required sequence), OPEN (low-stringency selection of peptide domains vs. triplet nucleotides followed by high-stringency selections of peptide combination vs. the final target in bacterial systems), and bacterial one-hybrid screening of zinc finger libraries, among others. ZFNs can also be designed and obtained commercially from e.g., Sangamo Biosciences™ (Richmond, CA).

Method for designing and obtaining TALENs are described in e.g. Reyon et al. Nature Biotechnology 2012 May; 30(5):460-5; Miller et al. Nat Biotechnol. (2011) 29: 143-148; Cermak et al. Nucleic Acids Research (2011) 39 (12): e82 and Zhang et al. Nature Biotechnology (2011) 29 (2): 149-53. A recently developed web-based program named Mojo Hand was introduced by Mayo Clinic for designing TAL and TALEN constructs for genome editing applications (can be accessed through www(dot)talendesign (dot)org). TALEN can also be designed and obtained commercially from e.g., Sangamo Biosciences™ (Richmond, CA).

The CRIPSR/Cas system for genome editing contains two distinct components: a gRNA and an endonuclease e.g. Cas9.

The gRNA is typically a 20 nucleotide sequence encoding a combination of the target homologous sequence (crRNA) and the endogenous bacterial RNA that links the crRNA to the Cas9 nuclease (tracrRNA) in a single chimeric transcript. The gRNA/Cas9 complex is recruited to the target sequence by the base-pairing between the gRNA sequence and the complement genomic DNA. For successful binding of Cas9, the genomic target sequence must also contain the correct Protospacer Adjacent Motif (PAM) sequence immediately following the target sequence. The binding of the gRNA/Cas9 complex localizes the Cas9 to the genomic target sequence so that the Cas9 can cut both strands of the DNA causing a double-strand break. Just as with ZFNs and TALENs, the double-stranded brakes produced by CRISPR/Cas can undergo homologous recombination or NHEJ.

The Cas9 nuclease has two functional domains: RuvC and HNH, each cutting a different DNA strand. When both of these domains are active, the Cas9 causes double strand breaks in the genomic DNA.

A significant advantage of CRISPR/Cas is that the high efficiency of this system coupled with the ability to easily create synthetic gRNAs enables multiple genes to be targeted simultaneously. In addition, the majority of cells carrying the mutation present biallelic mutations in the targeted genes.

However, apparent flexibility in the base-pairing interactions between the gRNA sequence and the genomic DNA target sequence allows imperfect matches to the target sequence to be cut by Cas9.

Modified versions of the Cas9 enzyme containing a single inactive catalytic domain, either RuvC- or HNH-, are called 'nickases'. With only one active nuclease domain, the Cas9 nickase cuts only one strand of the target DNA, creating a single-strand break or 'nick'. A single-strand break, or nick, is normally quickly repaired through the HDR pathway, using the intact complementary DNA strand as the template. However, two proximal, opposite strand nicks introduced by a Cas9 nickase are treated as a double-strand break, in what is often referred to as a 'double nick' CRISPR system. A double-nick can be repaired by either NHEJ or HDR depending on the desired effect on the gene target. Thus, if specificity and reduced off-target effects are crucial, using the Cas9 nickase to create a double-nick by designing two gRNAs with target sequences in close proximity and on opposite strands of the genomic DNA would decrease off-target effect as either gRNA alone will result in nicks that will not change the genomic DNA.

Modified versions of the Cas9 enzyme containing two inactive catalytic domains (dead Cas9, or dCas9) have no nuclease activity while still able to bind to DNA based on gRNA specificity. The dCas9 can be utilized as a platform for DNA transcriptional regulators to activate or repress gene expression by fusing the inactive enzyme to known regulatory domains. For example, the binding of dCas9 alone to a target sequence in genomic DNA can interfere with gene transcription.

There are a number of publically available tools available to help choose and/or design target sequences as well as lists of bioinformatically determined unique gRNAs for different genes in different species such as the Feng Zhang lab's Target Finder, the Michael Boutros lab's Target Finder (E-CRISP), the RGEN Tools: Cas-OFFinder, the CasFinder: Flexible algorithm for identifying specific Cas9 targets in genomes and the CRISPR Optimal Target Finder.

In order to use the CRISPR system, both gRNA and Cas9 should be expressed in a target cell. The insertion vector can contain both cassettes on a single plasmid or the cassettes are expressed from two separate plasmids. CRISPR plasmids are commercially available such as the px330 plasmid from Addgene.

"Hit and run" or "in-out"—involves a two-step recombination procedure. In the first step, an insertion-type vector containing a dual positive/negative selectable marker cassette is used to introduce the desired sequence alteration. The insertion vector contains a single continuous region of homology to the targeted locus and is modified to carry the mutation of interest. This targeting construct is linearized with a restriction enzyme at a one site within the region of homology, electroporated into the cells, and positive selection is performed to isolate homologous recombinants. These homologous recombinants contain a local duplication that is separated by intervening vector sequence, including the selection cassette. In the second step, targeted clones are subjected to negative selection to identify cells that have lost the selection cassette via intrachromosomal recombination between the duplicated sequences. The local recombination event removes the duplication and, depending on the site of recombination, the allele either retains the introduced mutation or reverts to wild type.

The end result is the introduction of the desired modification without the retention ofany exogenous sequences.

The "double-replacement" or "tag and exchange" strategy—involves a two-step selection procedure similar to the hit and run approach, but requires the use of two different targeting constructs. In the first step, a standard targeting vector with 3' and 5' homology arms is used to insert a dual positive/negative selectable cassette near the location where the mutation is to be introduced. After electroporation and positive selection, homologously targeted clones are identified. Next, a second targeting vector that contains a region of homology with the desired mutation is electroporated into targeted clones, and negative selection is applied to remove the selection cassette and introduce the mutation. The final allele contains the desired mutation while eliminating unwanted exogenous sequences.

Site-Specific Recombinases—The Cre recombinase derived from the P1 bacteriophage and Flp recombinase derived from the yeast *Saccharomyces cerevisiae* are site-specific DNA recombinases each recognizing a unique 34 base pair DNA sequence (termed "Lox" and "FRT", respectively) and sequences that are flanked with either Lox sites or FRT sites can be readily removed via site-specific recombination upon expression of Cre or Flp recombinase, respectively. For example, the Lox sequence is composed of an asymmetric eight base pair spacer region flanked by 13 base pair inverted repeats.

Cre recombines the 34 base pair lox DNA sequence by binding to the 13 base pair inverted repeats and catalyzing strand cleavage and relegation within the spacer region. The staggered DNA cuts made by Cre in the spacer region are separated by 6 base pairs to give an overlap region that acts as a homology sensor to ensure that only recombination sites having the same overlap region recombine.

Basically, the site specific recombinase system offers means for the removal of selection cassettes after homologous recombination. This system also allows for the generation of conditional altered alleles that can be inactivated or activated in a temporal or tissue-specific manner. Of note, the Cre and Flp recombinases leave behind a Lox or FRT "scar" of 34 base pairs. The Lox or FRT sites that remain are typically left behind in an intron or 3' UTR of the modified locus, and current evidence suggests that these sites usually do not interfere significantly with gene function.

Thus, Cre/Lox and Flp/FRT recombination involves introduction of a targeting vector with 3' and 5' homology arms containing the mutation of interest, two Lox or FRT sequences and typically a selectable cassette placed between the two Lox or FRT sequences. Positive selection is applied and homologous recombinants that contain targeted mutation are identified. Transient expression of Cre or Flp in conjunction with negative selection results in the excision of the selection cassette and selects for cells where the cassette has been lost. The final targeted allele contains the Lox or FRT scar of exogenous sequences.

Transposases—As used herein, the term "transposase" refers to an enzyme that binds to the ends of a transposon and catalyzes the movement of the transposon to another part of the genome.

As used herein the term "transposon" refers to a mobile genetic element comprising a nucleotide sequence, which can move around to different positions within the genome of a single cell. In the process the transposon can cause mutations and/or change the amount of a DNA in the genome of the cell.

A number of transposon systems that are able to also transpose in cells e.g. vertebrates have been isolated or designed, such as Sleeping Beauty [Izsvik and Ivics Molecular Therapy (2004) 9, 147-156], piggyBac [Wilson et al. Molecular Therapy (2007) 15, 139-145], Tol2 [Kawakami et al. PNAS (2000) 97 (21): 11403-11408] or Frog Prince [Miskey et al. Nucleic Acids Res. Dec. 1, (2003) 31(23): 6873-6881].

Generally, DNA transposons translocate from one DNA site to another in a simple, cut-and-paste manner. Each of these elements has their own advantages, for example, Sleeping Beauty is particularly useful in region-specific mutagenesis, whereas Tol2 has the highest tendency to integrate into expressed genes. Hyperactive systems are available for Sleeping Beauty and piggyBac. Most importantly, these transposons have distinct target site preferences, and can therefore introduce sequence alterations in overlapping, but distinct sets of genes. Therefore, to achieve the best possible coverage of genes, the use of more than one element is particularly preferred.

The basic mechanism is shared between the different transposases, therefore we will describe piggyBac (PB) as an example.

PB is a 2.5 kb insect transposon originally isolated from the cabbage looper moth, *Trichoplusia ni*. The PB transposon consists of asymmetric terminal repeat sequences that flank a transposase, PBase. PBase recognizes the terminal repeats and induces transposition via a "cut-and-paste" based mechanism, and preferentially transposes into the host genome at the tetranucleotide sequence TTAA. Upon insertion, the TTAA target site is duplicated such that the PB transposon is flanked by this tetranucleotide sequence. When mobilized, PB typically excises itself precisely to reestablish a single TTAA site, thereby restoring the host sequence to its pretransposon state. After excision, PB can transpose into a new location or be permanently lost from the genome.

Typically, the transposase system offers an alternative means for the removal of selection cassettes after homologous recombination quit similar to the use Cre/Lox or Flp/FRT. Thus, for example, the PB transposase system involves introduction of a targeting vector with 3' and 5' homology arms containing the mutation of interest, two PB terminal repeat sequences at the site of an endogenous TTAA sequence and a selection cassette placed between PB terminal repeat sequences. Positive selection is applied and homologous recombinants that contain targeted mutation are identified.

Transient expression of PBase removes in conjunction with negative selection results in the excision of the selection cassette and selects for cells where the cassette has been lost. The final targeted allele contains the introduced mutation with no exogenous sequences.

For PB to be useful for the introduction of sequence alterations, there must be a native TTAA site in relatively close proximity to the location where a particular mutation is to be inserted.

Genome editing using recombinant adeno-associated virus (rAAV) platform—this genome-editing platform is based on rAAV vectors, which enable insertion, deletion or substitution of DNA sequences in the genomes of live mammalian cells.

The rAAV genome is a single-stranded deoxyribonucleic acid (ssDNA) molecule, either positive- or negative-sensed, which is about 4.7 kb long. These single-stranded DNA viral vectors have high transduction rates and have a unique property of stimulating endogenous homologous recombination in the absence of double-strand DNA breaks in the genome. One of skill in the art can design a rAAV vector to target a desired genomic locus and perform both gross and/or subtle endogenous gene alterations in a cell. rAAV genome editing has the advantage in that it targets a single allele and does not result in any off-target genomic alterations. rAAV genome editing technology is commercially available, for example, the rAAV GENESIS™ system from Horizon™ (Cambridge, UK).

Methods for qualifying efficacy and detecting sequence alteration are well known in the art and include, but not limited to, DNA sequencing, electrophoresis, an enzyme-based mismatch detection assay and a hybridization assay such as PCR, RT-PCR, RNase protection, in-situ hybridization, primer extension, Southern blot, Northern Blot and dot blot analysis.

Sequence alterations in a specific gene can also be determined at the protein level using e.g. chromatography, electrophoretic methods, immunodetection assays such as ELISA and western blot analysis and immunohistochemistry.

Thus, according to some embodiments of the invention the pollen of the invention confers reduced fitness by way of partial genome incompatibility, parthenocarpy, stenospermocarpy, reduced shattering, inhibition of seed dormancy, cleistogamy, induced triploidy, conditional lethality, male sterility, female sterility, inducible promoters, complete sterility by nonflowering, reduced biotic/abiotic stress tolerance. The skilled artisan will know which method to select.

The nucleic acid construct of some embodiments of the invention can be utilized to stably or transiently transform plant cells. In stable transformation, the exogenous polynucleotide is integrated into the plant genome and as such it represents a stable and inherited trait. In transient transformation, the exogenous polynucleotide is expressed by the cell transformed but it is not integrated into the genome and as such it represents a transient trait.

There are various methods of introducing foreign genes into both monocotyledonous and dicotyledonous plants (Potrykus, I., Annu. Rev. Plant. Physiol., Plant. Mol. Biol. (1991) 42:205-225; Shimamoto et al., Nature (1989) 338: 274-276).

The principle methods of causing stable integration of exogenous DNA into plant genomic DNA include two main approaches:

(i) *Agrobacterium*-mediated gene transfer: Klee et al. (1987) Annu. Rev. Plant Physiol. 38:467-486; Klee and Rogers in Cell Culture and Somatic Cell Genetics of Plants, Vol. 6, Molecular Biology of Plant Nuclear Genes, eds. Schell, J., and Vasil, L. K., Academic Publishers, San Diego, Calif. (1989) p. 2-25; Gatenby, in Plant Biotechnology, eds. Kung, S. and Arntzen, C. J., Butterworth Publishers, Boston, Mass. (1989) p. 93-112.

(ii) Direct DNA uptake: Paszkowski et al., in Cell Culture and Somatic Cell Genetics of Plants, Vol. 6, Molecular Biology of Plant Nuclear Genes eds. Schell, J., and Vasil, L. K., Academic Publishers, San Diego, Calif. (1989) p. 52-68; including methods for direct uptake of DNA into protoplasts, Toriyama, K. et al. (1988) Bio/Technology 6:1072-1074. DNA uptake induced by brief electric shock of plant cells: Zhang et al. Plant Cell Rep. (1988) 7:379-384. Fromm et al. Nature (1986) 319:791-793. DNA injection into plant cells or tissues by particle bombardment, Klein et al. Bio/Technology (1988) 6:559-563; McCabe et al. Bio/Technology (1988) 6:923-926; Sanford, Physiol. Plant. (1990) 79:206-209; by the use of micropipette systems: Neuhaus et al., Theor. Appl. Genet. (1987) 75:30-36; Neuhaus and Spangenberg, Physiol. Plant. (1990) 79:213-217; glass fibers or silicon carbide whisker transformation of cell cultures, embryos or callus tissue, U.S. Pat. No. 5,464,765 or by the direct incubation of DNA with germinating pollen, DeWet et al. in Experimental Manipulation of Ovule Tissue, eds. Chapman, G. P. and Mantell, S. H. and Daniels, W. Longman, London, (1985) p. 197-209; and Ohta, Proc. Natl. Acad. Sci. USA (1986) 83:715-719.

The *Agrobacterium* system includes the use of plasmid vectors that contain defined DNA segments that integrate into the plant genomic DNA.

Methods of inoculation of the plant tissue vary depending upon the plant species and the *Agrobacterium* delivery system. A widely used approach is the leaf disc procedure, which can be performed with any tissue explant that provides a good source for initiation of whole plant differentiation. See, e.g., Horsch et al. in Plant Molecular Biology Manual A5, Kluwer Academic Publishers, Dordrecht (1988) p. 1-9. A supplementary approach employs the *Agrobacterium* delivery system in combination with vacuum infiltration. The *Agrobacterium* system is especially viable in the creation of transgenic dicotyledonous plants.

There are various methods of direct DNA transfer into plant cells. In electroporation, the protoplasts are briefly exposed to a strong electric field. In microinjection, the DNA is mechanically injected directly into the cells using very small micropipettes. In microparticle bombardment, the DNA is adsorbed on microprojectiles such as magnesium sulfate crystals or tungsten particles, and the microprojectiles are physically accelerated into cells or plant tissues.

Following stable transformation plant propagation is exercised. The most common method of plant propagation is by seed. Regeneration by seed propagation, however, has the deficiency that due to heterozygosity there is a lack of uniformity in the crop, since seeds are produced by plants according to the genetic variances governed by Mendelian rules. Basically, each seed is genetically different and each will grow with its own specific traits. Therefore, it is preferred that the transformed plant be produced such that the regenerated plant has the identical traits and characteristics of the parent transgenic plant. Therefore, it is preferred that the transformed plant be regenerated by micropropagation which provides a rapid, consistent reproduction of the transformed plants.

Micropropagation is a process of growing new generation plants from a single piece of tissue that has been excised from a selected parent plant or cultivar. This process permits the mass reproduction of plants having the preferred tissue expressing the fusion protein. The new generation plants which are produced are genetically identical to, and have all of the characteristics of, the original plant.

Micropropagation allows mass production of quality plant material in a short period of time and offers a rapid multiplication of selected cultivars in the preservation of the characteristics of the original transgenic or transformed plant.

The advantages of cloning plants are the speed of plant multiplication and the quality and uniformity of plants produced.

Micropropagation is a multi-stage procedure that requires alteration of culture medium or growth conditions between stages. Thus, the micropropagation process involves four basic stages: Stage one, initial tissue culturing; stage two, tissue culture multiplication; stage three, differentiation and plant formation; and stage four, greenhouse culturing and hardening. During stage one, initial tissue culturing, the tissue culture is established and certified contaminant-free. During stage two, the initial tissue culture is multiplied until a sufficient number of tissue samples are produced from the seedlings to meet production goals. During stage three, the tissue samples grown in stage two are divided and grown into individual plantlets. At stage four, the transformed plantlets are transferred to a greenhouse for hardening where the plants' tolerance to light is gradually increased so that it can be grown in the natural environment.

According to some embodiments of the invention, the transgenic plants are generated by transient transformation of leaf cells, meristematic cells or the whole plant.

Transient transformation can be effected by any of the direct DNA transfer methods described above or by viral infection using modified plant viruses.

Viruses that have been shown to be useful for the transformation of plant hosts include CaMV, Tobacco mosaic virus (TMV), brome mosaic virus (BMV) and Bean Common Mosaic Virus (BV or BCMV). Transformation of plants using plant viruses is described in U.S. Pat. No. 4,855,237 (bean golden mosaic virus; BGV), EP-A 67,553 (TMV), Japanese Published Application No. 63-14693 (TMV), EPA 194,809 (BV), EPA 278,667 (BV); and Gluzman, Y. et al., Communications in Molecular Biology: Viral Vectors, Cold Spring Harbor Laboratory, New York, pp. 172-189 (1988). Pseudovirus particles for use in expressing foreign DNA in many hosts, including plants are described in WO 87/06261.

According to some embodiments of the invention, the virus used for transient transformations is avirulent and thus is incapable of causing severe symptoms such as reduced growth rate, mosaic, ring spots, leaf roll, yellowing, streaking, pox formation, tumor formation and pitting. A suitable avirulent virus may be a naturally occurring avirulent virus or an artificially attenuated virus.

Virus attenuation may be effected by using methods well known in the art including, but not limited to, sub-lethal heating, chemical treatment or by directed mutagenesis techniques such as described, for example, by Kurihara and Watanabe (Molecular Plant Pathology 4:259-269, 2003), Gal-on et al. (1992), Atreya et al. (1992) and Huet et al. (1994).

Suitable virus strains can be obtained from available sources such as, for example, the American Type culture Collection (ATCC) or by isolation from infected plants. Isolation of viruses from infected plant tissues can be effected by techniques well known in the art such as described, for example by Foster and Taylor, Eds. "Plant Virology Protocols: From Virus Isolation to Transgenic Resistance (Methods in Molecular Biology (Humana Pr), Vol 81)", Humana Press, 1998. Briefly, tissues of an infected plant believed to contain a high concentration of a suitable virus, preferably young leaves and flower petals, are ground in a buffer solution (e.g., phosphate buffer solution) to produce a virus infected sap which can be used in subsequent inoculations.

Construction of plant RNA viruses for the introduction and expression of non-viral exogenous polynucleotide sequences in plants is demonstrated by the above references as well as by Dawson, W. O. et al., Virology (1989) 172:285-292; Takamatsu et al. EMBO J. (1987) 6:307-311; French et al. Science (1986) 231:1294-1297; Takamatsu et al. FEBS Letters (1990) 269:73-76; and U.S. Pat. No. 5,316,931.

When the virus is a DNA virus, suitable modifications can be made to the virus itself. Alternatively, the virus can first be cloned into a bacterial plasmid for ease of constructing the desired viral vector with the foreign DNA. The virus can then be excised from the plasmid. If the virus is a DNA virus, a bacterial origin of replication can be attached to the viral DNA, which is then replicated by the bacteria.

Transcription and translation of this DNA will produce the coat protein, which will encapsidate the viral DNA. If the virus is an RNA virus, the virus is generally cloned as a cDNA and inserted into a plasmid. The plasmid is then used to make all of the constructions. The RNA virus is then produced by transcribing the viral sequence of the plasmid and translation of the viral genes to produce the coat protein(s) which encapsidate the viral RNA.

In one embodiment, a plant viral polynucleotide is provided in which the native coat protein coding sequence has been deleted from a viral polynucleotide, a non-native plant viral coat protein coding sequence and a non-native promoter, preferably the subgenomic promoter of the non-native coat protein coding sequence, capable of expression in the plant host, packaging of the recombinant plant viral polynucleotide, and ensuring a systemic infection of the host by the recombinant plant viral polynucleotide, has been inserted. Alternatively, the coat protein gene may be inactivated by insertion of the non-native polynucleotide sequence within it, such that a protein is produced. The recombinant plant viral polynucleotide may contain one or more additional non-native subgenomic promoters.

Each non-native subgenomic promoter is capable of transcribing or expressing adjacent genes or polynucleotide sequences in the plant host and incapable of recombination with each other and with native subgenomic promoters. Non-native (foreign) polynucleotide sequences may be inserted adjacent the native plant viral subgenomic promoter or the native and a non-native plant viral subgenomic promoters if more than one polynucleotide sequence is included. The non-native polynucleotide sequences are transcribed or expressed in the host plant under control of the subgenomic promoter to produce the desired products.

In a second embodiment, a recombinant plant viral polynucleotide is provided as in the first embodiment except that the native coat protein coding sequence is placed adjacent one of the non-native coat protein subgenomic promoters instead of a non-native coat protein coding sequence.

In a third embodiment, a recombinant plant viral polynucleotide is provided in which the native coat protein gene is adjacent its subgenomic promoter and one or more non-native subgenomic promoters have been inserted into the viral polynucleotide. The inserted non-native subgenomic promoters are capable of transcribing or expressing adjacent genes in a plant host and are incapable of recombination with each other and with native subgenomic promoters. Non-native polynucleotide sequences may be inserted adjacent the non-native subgenomic plant viral promoters such that the sequences are transcribed or expressed in the host plant under control of the subgenomic promoters to produce the desired product.

In a fourth embodiment, a recombinant plant viral polynucleotide is provided as in the third embodiment except that the native coat protein coding sequence is replaced by a non-native coat protein coding sequence.

The viral vectors are encapsidated by the coat proteins encoded by the recombinant plant viral polynucleotide to produce a recombinant plant virus. The recombinant plant viral polynucleotide or recombinant plant virus is used to infect appropriate host plants. The recombinant plant viral polynucleotide is capable of replication in the host, systemic spread in the host, and transcription or expression of foreign gene(s) (exogenous polynucleotide) in the host to produce the desired protein.

Techniques for inoculation of viruses to plants may be found in Foster and Taylor, eds. "Plant Virology Protocols: From Virus Isolation to Transgenic Resistance (Methods in Molecular Biology (Humana Pr), Vol 81)", Humana Press, 1998; Maramorosh and Koprowski, eds. "Methods in Virology" 7 vols, Academic Press, New York 1967-1984; Hill, S. A. "Methods in Plant Virology", Blackwell, Oxford, 1984; Walkey, D. G. A. "Applied Plant Virology", Wiley, New York, 1985; and Kado and Agrawa, eds. "Principles and Techniques in Plant Virology", Van Nostrand-Reinhold, New York.

In addition to the above, the polynucleotide of the present invention can also be introduced into a chloroplast genome thereby enabling chloroplast expression.

A technique for introducing exogenous polynucleotide sequences to the genome of the chloroplasts is known. This technique involves the following procedures. First, plant cells are chemically treated so as to reduce the number of chloroplasts per cell to about one. Then, the exogenous polynucleotide is introduced via particle bombardment into the cells with the aim of introducing at least one exogenous polynucleotide molecule into the chloroplasts. The exogenous polynucleotides selected such that it is integratable into the chloroplast's genome via homologous recombination which is readily effected by enzymes inherent to the chloroplast. To this end, the exogenous polynucleotide includes, in addition to a gene of interest, at least one polynucleotide stretch, which is derived from the chloroplast's genome. In addition, the exogenous polynucleotide includes a selectable marker, which serves by sequential selection procedures to ascertain that all or substantially all of the copies of the chloroplast genomes following such selection will include the exogenous polynucleotide.

Further details relating to this technique are found in U.S. Pat. Nos. 4,945,050; and 5,693,507 which are incorporated herein by reference. A polypeptide can thus be produced by the protein expression system of the chloroplast and become integrated into the chloroplast's inner membrane.

Specific methods for weed transformation are described in Jofre-Garfias et al., 1997, Swain et al., 2010 and Pal et al., 2013, each of which is incorporated by reference in its entirety. According to a further aspect of the invention there is provided a method of producing pollen, the method comprising:

(a) growing weed producing pollen that reduces fitness of at least one weed species of interest; and (b) harvesting the pollen.

Thus the pollen product producing weed is grown in dedicated settings, e.g., open or closed settings, e.g., a greenhouse. According to a specific embodiment, the growth environment for the manufacture of the pollen does not include crop plants or the weed species of interest. For example, the growth area includes a herbicide susceptible weed variant but not a herbicide resistant weed variant (of the same species). Another example, the growth environment comprises a GM weed with a destructor gene the weed being fertile and producing pollen, but doesn't include the weed in which the destructor gene is expressed.

According to a specific embodiment, growing the weed producing pollen that reduces fitness is effected in a large scale setting (e.g., hundreds to thousands m2).

According to some embodiments of the invention, the weed producing pollen comprises only male plants.

Harvesting pollen is well known in the art. For example, by the use of paper bags. Another example is taught in U.S. 20060053686, which is hereby incorporated by reference in its entirety.

Once pollen is obtained it can be stored for future use. Examples of storage conditions include, but are not; limited to, storage temperatures in Celsius degrees e.g., −196, −160, −130, −80, −20, −5, 0, 4, 20, 25, 30 or 35; percent of relative humidity e.g., 0, 10, 20, 30, 40, 50, 60, 70, 80, 90 or 100. Control over humidity can be achieved by using a dehydrating agent as known in the art. Additionally, the pollen can be stored in light or dark.

Alternatively, the pollen product of the present teachings is subjected to a post harvest treatment.

Thus, according to an aspect of the invention there is provided a method of producing pollen for use in artificial pollination, the method comprising:

(a) obtaining pollen that reduces fitness of at least one weed species of interest, e.g., as described herein; and (b) treating the pollen for use in artificial pollination.

Accordingly, there is provided a composition of matter comprising weed pollen that reduces fitness of at least one weed species of interest, the pollen having been treated for improving its use in artificial pollination.

Examples of such treatments include, but are not limited to coating, priming, formulating, chemical inducers, physical inducers [e.g., potential inducers include, but are not limited to, ethanol, hormones, steroids, (e.g., dexamethasone, glucocorticoid, estrogen, estradiol), salicylic acid, pesticides and metals such as copper, antibiotics such as but not limited to tetracycline, Ecdysone, ACEI, Benzothiadiazole and Safener, Tebufenozide or Methoxyfenozide], solvent solubilization, drying, heating, cooling and irradiating (e.g., gamma, UV, X-ray, particle).

In some embodiments, the pollen composition of the present invention contains dehydrated or partially dehydrated pollen.

Thus, the pollen composition may comprise a surfactant, a stabilizer, a buffer, a preservative, an antioxidant, an extender, a solvent, an emulsifier, an invert emulsifier, a spreader, a sticker, a penetrant, a foaming agent, an anti-foaming agent, a thickener, a safener, a compatibility agent, a crop oil concentrate, a viscosity regulator, a binder, a tacker, a drift control agent, a fertilizer, a timed-release coating, a water-resistant coating, an antibiotic, a fungicide, a nematicide, a herbicide or a pesticide.

Other ingredients and further description of the above ingredients is provided hereinbelow.

Under ordinary conditions of storage and use, the composition of the present invention may contain a preservative to prevent the growth of microorganisms.

The preventions of the action of microorganisms can be brought about by various antibacterial and antifungal agents, for example, parabens, chlorobutanol, sorbic acid, and the like. Antioxidants may also be added to the pollen suspension to preserve the pollen from oxidative damage during storage. Suitable antioxidants include, for example, ascorbic acid, tocopherol, sulfites, metabisulfites such as potassium metabisulfite, butylhydroxytoluene, and butylhydroxyanisole.

Thus, pollen compositions that may also be used but not limited to mixtures with various agricultural chemicals and/or herbicides, insecticides, miticides and fungicides, pesticidal and biopesticidal agents, nematocides, bactericides, acaricides, growth regulators, chemosterilants, semiochemicals, repellents, attractants, pheromones, feeding stimulants or other biologically active compounds all of which can be added to the pollen to form a multi-component composition giving an even broader spectrum of agricultural protection.

Thus in the artificial pollination method of the present invention can be applied together with the following herbicides but not limited to: ALS inhibitor herbicide, auxin-like herbicides, glyphosate, glufosinate, sulfonylureas, imidazolinones, bromoxynil, delapon, dicamba, cyclohezanedione, protoporphyrionogen oxidase inhibitors, 4-hydroxyphenyl-pyruvate-dioxygenase inhibitors herbicides.

In some embodiments, the pollen can be combined with appropriate solvents or surfactants to form a formulation. Formulations enable the uniform distribution of a relatively small amount of the pollen over a comparatively large growth area. In addition to providing the user with a form of a pollen that is easy to handle, formulating can enhance its fertilization activity, improve its ability to be applied to a plant, enable the combination of aqueous-soluble and organic-soluble compounds, improve its shelf-life, and protect it from adverse environmental conditions while in storage or transit.

Numerous formulations are known in the art and include, but are not limited to, solutions, soluble powders, emulsifiable concentrates, wettable powders, liquid flowables, and dry flowables. Formulations vary according to the solubility of the active or additional formulation ingredients in water, oil and organic solvents, and the manner the formulation is applied (i.e., dispersed in a carrier, such as water, or applied as a dry formulation).

Hence, contemplated are wet (e.g., liquid) as well as dry formulations.

Solution formulations are designed for those active ingredients that dissolve readily in water or other non-organic solvents such as methanol. The formulation is a liquid and comprises of the active ingredient and additives.

Suitable liquid carriers, such as solvents, may be organic or inorganic. Water is one example of an inorganic liquid carrier. Organic liquid carriers include vegetable oils and epoxidized vegetable oils, such as rape seed oil, castor oil, coconut oil, soybean oil and epoxidized rape seed oil, epoxidized castor oil, epoxidized coconut oil, epoxidized soybean oil, and other essential oils. Other organic liquid carriers include aromatic hydrocarbons, and partially hydrogenated aromatic hydrocarbons, such as alkylbenzenes containing 8 to 12 carbon atoms, including xylene mixtures, alkylated naphthalenes, or tetrahydronaphthalene. Aliphatic or cycloaliphatic hydrocarbons, such as paraffins or cyclohexane, and alcohols, such as ethanol, propanol or butanol, also are suitable organic carriers. Gums, resins, and rosins used in forest products applications and naval stores (and their derivatives) also may be used. Additionally, glycols, including ethers and esters, such as propylene glycol, dipropylene glycol ether, diethylene glycol, 2-methoxyethanol, and 2-ethoxyethanol, and ketones, such as cyclohexanone, isophorone, and diacetone alcohol may be used. Strongly polar organic solvents include N-methylpyrrolid-2-one, dimethyl sulfoxide, and N,N-dimethylformamide.

Soluble powder formulations are similar to solutions in that, when mixed with water, they dissolve readily and form a true solution. Soluble powder formulations are dry and include the active ingredient and additives.

Emulsifiable concentrate formulations are liquids that contain the active ingredient, one or more solvents, and an emulsifier that allows mixing with a component in an organic liquid carrier. Formulations of this type are highly concentrated, relatively inexpensive per pound of active ingredient, and easy to handle, transport, and store. In addition, they require little agitation (will not settle out or separate) and are not abrasive to machinery or spraying equipment.

Wettable powders are dry, finely ground formulations in which the active ingredient is combined with a finely ground carrier (usually mineral clay), along with other ingredients to enhance the ability of the powder to suspend in water. Generally, the powder is mixed with water for application. Typical solid diluents are described in Watkins et al., Handbook of Insecticide Dust Diluents and Carriers, 2nd Ed., Dorland Books, Caldwell, N.J. The more absorptive diluents are preferred for wettable powders and the denser ones for dusts.

Liquid flowable formulations are made up of finely ground active ingredient suspended in a liquid. Dry flowable and water-dispersible granule formulations are much like wettable powders except that the active ingredient is formulated on a large particle (granule) instead of onto a ground powder.

The methods of making such formulations are well known. Solutions are prepared by simply mixing the ingredients. Fine, solid compositions are made by blending and, usually, grinding, as in a hammer or fluid energy mill. Suspensions are prepared by wet-milling (see, for example, U.S. Pat. No. 3,060,084).

The concentration of a pollen growth stimulating compound in a formulation may vary according to particular compositions and applications.

In some embodiments of the disclosure, inactive ingredients i.e., adjuvants) are added to pollen to improve the performance of the formulation. For example, in one embodiment of the disclosure, pollen is formulated with a surfactant. A surfactant (surface active agent) is a type of adjuvant formulated to improve the dispersing/emulsifying, absorbing, spreading, and sticking properties of a spray mixture. Surfactants can be divided into the following five groupings: (1) non-ionic surfactants, (2) crop oil concentrates, (3) nitrogen-surfactant blends, (4) esterified seed oils, and (5) organo-silicones.

Suitable surfactants may be nonionic, cationic, or anionic, depending on the nature of the compound used as an active ingredient. Surfactants may be mixed together in some embodiments of the disclosure. Nonionic surfactants include polyglycol ether derivatives of aliphatic or cycloaliphatic alcohols, saturated or unsaturated fatty acids and alkylphenols. Fatty acid esters of polyoxyethylene sorbitan, such as polyoxyethylene sorbitan trioleate, also are suitable nonionic surfactants. Other suitable nonionic surfactants include water-soluble polyadducts of polyethylene oxide with polypropylene glycol, ethylenediaminopolypropylene glycol and alkylpolypropylene glycol. Particular nonionic surfactants include nonylphenol polyethoxyethanols, polyethoxylated castor oil, polyadducts of polypropylene and polyethylene oxide, tributylphenol polyethoxylate, polyethylene glycol and octylphenol polyethoxylate. Cationic surfactants include quaternary ammonium salts carrying, as N-substituents, an 8 to 22 carbon straight or branched chain alkyl radical.

The quaternary ammonium salts carrying may include additional substituents, such as unsubstituted or halogenated lower alkyl, benzyl, or hydroxy-lower alkyl radicals. Some such salts exist in the form of halides, methyl sulfates, and ethyl sulfates. Particular salts include stearyldimethylammonium chloride and benzyl bis (2-chloroethyl) ethylammonium bromide.

Suitable anionic surfactants may be water-soluble soaps as well as water-soluble synthetic surface-active compounds. Suitable soaps include alkali metal salts, alkaline earth metal salts, and unsubstituted or substituted ammonium salts of higher fatty acids. Particular soaps include the sodium or potassium salts of oleic or stearic acid, or of natural fatty acid mixtures. Synthetic anionic surfactants include fatty sulfonates, fatty sulfates, sulfonated benzimidazole derivatives, and alkylarylsulfonates. Particular synthetic anionic surfactants include the sodium or calcium salt of ligninsulfonic acid, of dodecyl sulfate, or of a mixture of fatty alcohol sulfates obtained from natural fatty acids. Additional examples include alkylarylsulfonates, such as sodium or calcium salts of dodecylbenzenesulfonic acid, or dibutylnaphthalenesulfonic acid. Corresponding phosphates for such anionic surfactants are also suitable.

Other adjuvants include carriers and additives, for example, wetting agents, such as anionic, cationic, nonionic, and amphoteric surfactants, buffers, stabilizers, preservatives, antioxidants, extenders, solvents, emulsifiers, invert emulsifiers, spreaders, stickers, penetrants, foaming agents, anti-foaming agents, thickeners, safeners, compatibility agents, crop oil concentrates, viscosity regulators, binders, tackers, drift control agents, or other chemical agents, such as fertilizers, antibiotics, fungicides, nematicides, or pesticides (others are described hereinabove). Such carriers and additives may be used in solid, liquid, gas, or gel form, depending on the embodiment and its intended application.

As used herein "artificial pollination" is the application, by hand or dedicated machinery, of fertile stigmas with the pollen from plants with desired characteristics, as described herein.

Artificial pollination in the field can be achieved by pollen spraying (e.g., wet or dry spray formulations), spreading, dispersing or any other method. The application itself will be performed by ground equipment, aircraft, unmanned aerial vehicles (UAV), remote-piloted vehicles(RPV), drones or specialized robots, special vehicles or tractors, animal assisted, specialized apparatus that is designed to spread boosts of pollen, specialized apparatus that combines ventilation and spraying of pollen to enhance recycling of pollen or any other application method or apparatus wherein application can be of a single dose, multiple doses, continuous, on an hourly/daily/weekly/monthly basis or any other application timing methodology.

It will be appreciated that at any time the weed of interest can be further treated with other weed control means. For example, the weed may be treated with a herbicide (which is usually applied at early stages of germination as opposed to the pollen, which is applied at flowering). Thus a herbicide for instance can be applied prior to, concomitantly with or following pollen treatment.

Any of the pollen compositions described herein can be produced as a single species pollen with a single trait for reducing weed fitness, a single species pollen with a plurality of traits for reducing weed fitness (e.g., a number of different herbicide resistances or a number of sterility encoding mechanisms) all introduced into a single weed or to a plurality of weeds of the same species, a multispecies pollen with a single trait or a multispecies pollen with a plurality of said traits.

Thus, commercial products can be manufactured as kits whereby each pollen type is packed in a separate packaging means (e.g., bag), or two or more types (e.g., weed species and/or different treatments) of pollen are combined into a single composition and packed in a single packaging means (e.g., bag). The product may be accompanied by instructions for use, regulatory information, product description and the like.

The kit may also include in a separate packaging means other active ingredients such as at least one of a chemical inducer (as described above), herbicide, fertilizer, antibiotics and the like.

As used herein the term "about" refers to ±10%.

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

EXAMPLES

Reference is now made to the following examples, which together with the above descriptions illustrate some embodiments of the invention in a non limiting fashion.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Maryland (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes I-III Cellis, J. E., ed. (1994); "Current Protocols in Immunology" Volumes I-III Coligan J. E., ed. (1994); Stites et al. (eds), "Basic and Clinical Immunology" (8th Edition), Appleton & Lange, Norwalk, C T (1994); Mishell and Shiigi (eds), "Selected Methods in Cellular Immunology", W. H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., Eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, C A (1990); Marshak et al., "Strategies for Protein Purification and Characterization—A Laboratory Course Manual" CSHL Press (1996); all of which are incorporated by reference as if fully set forth herein. Other general references are provided throughout this document. The procedures therein are believed to be well known in the art and are provided for the convenience of the reader. All the information contained therein is incorporated herein by reference.

Example 1

Weed Control Following Artificial Pollination with Different Intervals Between Applications in *A. palmeri*

Twelve female *A. palmeri* plants from 4 different genetic sources that were in their early flowering stage (up to two weeks from the development of the first receptive stigma on the female plant) were arranged in a net house in a 3 boxes structure. Each box contained 4 *A. palmeri* female plants and a flowering male plant was placed in the middle. To allow competition from natural pollen shed from male plants.

Pollen for the treatment was produced from males that were grown in a separate location by the following procedure: Pollen was harvested for 3 consecutive days and was stored at 4° C. until it was X-ray irradiated with a dose of 300 Gy (1 day before the first application). After the irradiation treatment the pollen was stored again at 4° C. until used. A second batch of pollen was harvested for 2 consecutive days during the experiment and was treated similarly. The second batch of pollen was used for the last day of artificial pollination.

Artificial pollinations were conducted for 7 days. Three different artificial pollination regimens were examined: i). Every day (except for Saturday, i.e. 6 applications); ii). Every 3 days (3 applications); and iii). Every 6 days (in the first and seventh day, 2 applications) See Table 4 below. All treatment regimens were randomly distributed in all 3 boxes. Artificial pollination procedures were conducted around 06:00 AM in the morning before natural pollen shedding by the male plants. Male plants were removed from the net house 2 hours after the last artificial pollination was conducted. Following completion of pollination from either natural male shedding or artificial pollination female plants were grown for additional 16 days to allow full seed maturation and then seeds were harvested.

From each female plant, 2 lateral spikes were harvested and from these spikes seeds were harvested. Seeds were separated by their weight using an air blower apparatus that differentiates between normal seeds (with normal weight) and aborted seeds (with low weight). The number of seeds in each group was counted and the percentages of normal seeds in each regime was assessed (see results in Table 4 below).

TABLE 4

| Treatment | Day | | | | | | |
|---|---|---|---|---|---|---|---|
| regimen | 1 | 2 | 3 | 4 | 5 | 6 | 7 |
| Every day | ✓ | ✓ | | ✓ | ✓ | ✓ | ✓ |
| Every 3 days | ✓ | | | ✓ | | | ✓ |

TABLE 4-continued

| Treatment regimen | Day 1 | 2 | 3 | 4 | 5 | 6 | 7 |
|---|---|---|---|---|---|---|---|
| Every 6 days | ✓ | | | | | | ✓ |

TABLE 5

| Artificial pollination regime | Average number of normal seeds | Average number of aborted seeds | SDE number of good seeds | SDE number of aborted seeds |
|---|---|---|---|---|
| Every 6 days | 23.5 | 412.5 | 10.9 | 73.7 |
| every 3 days | 12.375 | 330.375 | 3.8 | 67.5 |
| every day | 7.75 | 500 | 3.4 | 137.2 |

TABLE 6

| Side spikes | Average % of normal seeds | Average % of aborted seeds |
|---|---|---|
| Every 6 days | 5.58 | 94.42 |
| Every 3 days | 3.83 | 96.17 |
| Every day | 2.66 | 97.34 |

No significant difference was found between the number of normal seeds in each of the pollination regimens when using t-test. The results show that in all three regimens more than 94% of the seeds that were obtained are aborted seeds.

Example 2

Artificial Pollination with Different Amount of Pollen in *A. palmeri* in Growth Room The experiment goal was to evaluate the minimum pollen amount needed to achieve maximal pollination efficiency. Eight *A. palmeri* female plants that were grown in net house were placed in a growth room in 34° C./24° C., 16/8 h day/night conditions three days prior to the experiment. Pollen was harvested in morning hours from male *A. palmeri* plants that were grown in a separate growth room in 28° C./22° C., 16/8h day/night conditions. Four different pollen amounts were examined and was mixed with talc in order to keep the total amount of powder constant in each pollination treatment. The mixtures that were examined are: i) 120 mg pollen+80 mg talc ii) 80 mg pollen+120 mg talc iii) 40 mg pollen+160 mg talc and iv) 20 mg pollen+180 mg talc. Each examined mixture was tested on 2 *A. palmeri* female plants (i.e. 2 replicas for each treatment). As *A. palmeri* female plants are highly variable in their reproduction capabilites (namely in the amount of seeds they produce) 3 spikes were selected on each female plant and each of these spikes was artificially pollinated using paper tube (diameter of ~1 cm and 20 cm length) with 5 mg of pollen inside. These spikes were used as normalizers for female reproduction potential. Sixteen days after the artificial pollination event the experiment was harvested. From each female plant 6 spikes were harvested: 3 normalizer spikes+3 examined spikes (for each normalizer spike an additional spike with similar position on the plant and similar length was chosen and reffered here as the examined spike). The spikes were dryed for 2 days and then seeds were manually extrcted and total seed weight was measured and recorded. The average and SDE of the normalized total seed weight in each condition of artificial pollination appears in the following Table 7.

TABLE 7

| | 120 mg pollen + 80 mg Talc | 80 mg pollen + 120 mg Talc | 40 mg pollen + 160 mg Talc | 20 mg pollen + 180 Talc |
|---|---|---|---|---|
| AVG | 1.44 | 1.02 | 1.39 | 1.27 |
| SDE | 0.26 | 0.10 | 0.26 | 0.31 |
| P-value* | NA | 0.134 | 0.891 | 0.667 |

*P-value of t-test between the treatment of 120 mg pollen + 80 mg Talc and the other treatments It can be seen from the results that the average total seed weight did not change significantly between all conditions, namely pollen amount of 120 mg as well as 20 mg yield similar pollination efficiency (the amounts are per plant per application).

Example 3

Achieve Efficient Artificial Pollination in *A. palmeri* with Different Amounts of Pollen During morning hours *A. palmeri* pollen was collected from male plants that were grown in a greenhouse during February in Israel at Rehovot region, Israel. The collected pollen was tested for viability using TTC staining (Brown, 1954; Oberle & Watson, 1953; Norton, 1966) and in-vitro pollen tube germination (Shauck, PhD Thesis, University of Missouri 2014, Identification of nontarget-site mechanisms of glyphosate resistance in roots and pollen of *amaranthus* and *ambrosia*).

Twelve *A. palmeri* female plants that were grown in a separate greenhouse were used in this experiment.

In the experiment, 4 pollen:Talc ratios were examined while the total amount of dry material was constant and was equal to 300 mg. The examined 4 pollen:Talc ratios were: 1. 80 mg:220 mg 2. 40 mg:260 mg 3. 20 mg:280 mg and 4. 10 mg:290 mg. Each treatment was examined on 3 repeats (namely, on 3 female *A. palmeri* plants). Each pollen:Talc mixture was applied on the females using a small sprayer and 3 spikes were selected on each female that would serve as the examined spikes. *A. palmeri* female plants have very high variance in their fertility, which is reflected in high variance in the number of seeds they produce per spike. Therefore, for each examined spike, an additional spike was selected that was similar in size and location on the female plant, this spike served as a normalizer. These normalizer spikes were artificially pollinated using paper tubes with 10 mg of only pollen inside and they were covered during the pollen:talc mixtures spraying. Additionally, on each female plant 2 additional spikes were selected that were covered with empty paper tubes while the artificial pollination was conducted and served as blank control in order to evaluate the pollen contamination level. Sixteen days after the pollination event, all examined and normalizer spikes were cut and all seeds were harvested. Total seed weight per each spike was measured and normalized by the weight of the total seeds from the corresponding normalizer spike. The average and standard deviation of these normalized values for each pollen:Talc ratio is depicted in Table 8 below. It can be seen although amount of pollen was reduced from 80 mg to 10 mg no significant reduction in the amount of seeds per spike were obtained indicating that these amounts are equally efficient for artificial pollination.

TABLE 8

| Pollen:Talc | Average seed weight (mg) | Average seed weight in Normalizers (mg) | Normalized seed weight | SD | t-test vs 80 mg pollen:220 mg Talc |
|---|---|---|---|---|---|
| 10 mg:290 mg | 78.00 | 96.89 | 0.81 | 0.06 | 0.56 |
| 20 mg:280 mg | 64.11 | 71.44 | 0.90 | 0.34 | 0.72 |
| 40 mg:260 mg | 88.00 | 82.78 | 1.06 | 0.39 | 0.30 |
| 80 mg:220 mg | 51.22 | 56.78 | 0.90 | 0.29 | — |

REFERENCES

W. V. Brown, "A preliminary study of the staining of plant cells by tetrazolium chloride," Bulletin of the Torrey Botanical Club, vol. 81, no. 2, pp. 127-136, 1954.

D. G. Oberle and R. Watson, "The use of 2,3,5 triphenyl tetrazolium chloride (TTC) in viability test of fruit pollen," Journal of the American Society for Horticultural Science, vol. 61, pp. 299-303, 1953.

J. Norton D, "Testing of plum pollen viability with tetrazolium salts," American Society for Horticultural Science, vol. 89, pp. 132-134, 1966.

Example 4

Achieve Efficient Seedbank Control Using Artificial Pollination with X-Ray Irradiated Pollen in *A. palmeri* Under Field Conditions The experiment was conducted in Rehovot region, Israel during the summer season. The experiment included 16 plots, each of size 5×5 m, with 4 m of inter-plot borders of dense corn, which were used to minimize pollen contamination between the plots. Corn was sown at the border regions at high density of 10-12 plants/meter and two weeks after corn was sown inside the plots at a density of 6-8 plants/meter. Eight days later, *A. palmeri* seeds were sown inside the plots to achieve a final density of 1 plant every 90 cm (4 seeds were sown in each hole and were thinned after germination).

The experiment included 4 treatment regimens: 1) No-treatment control 2) Application of X-ray irradiated pollen every 3-days (3D) 3) Application of X-ray irradiated pollen every week and 4) Application of X-ray irradiated pollen every two weeks. Each treatment was applied in 4 plots that were randomly distributed between all the 16 plots.

On June 14$^{th}$ the first pollen treatment was applied in the every 3-days regimen plots. On June 21$^{st}$ the first pollen treatment was applied in the every-week regimen plots. On June 26$^{th}$ the first pollen treatment was applied in the every-two weeks regimen plots. No additional pollen was applied in the control plots—these plots were pollinated by natural pollination only.

The treated pollen that was used for all applications was collected from *A. palmeri* male plants that were grown in a separate net-house and was collected during morning hours for several consecutive days (according to the pollen needed amount) and was X-ray irradiated with a dose of 300Gy.

The artificial pollination was conducted using a pollen mini-duster machine (kiwi pollen mini-duster www(dot)kiwipollen(dot)com/dry-applicators/) and pollen was mixed with Talc at a ratio of 1:1 or 2:1 in order to reduce amounts of pollen used per artificial pollination. The pollination procedure was conducted in a way that all *A. palmeri* female inflorescences were sprayed with the treated pollen mixture. During the flowering season palmer plants are still growing in size and thus, the number of inflorescences and their size increase. Therefore, an increasing amount of pollen was used to cover all the inflorescences. Therefore, the average amount of pollen used per plot per treatment was not constant and ranged from 0.625 g to 10 g per the above mentioned-density.

On August 16$^{th}$ last pollen treatment was applied to all the treated plots. After 2 hours all *A. palmeri* male plants were harvested and *A. palmeri* female plants continued growing for additional 16 days in order to allow all the seeds to reach full maturity.

The following Table 9 summarizes the total number of applications that was applied in each treatment interval.

TABLE 9

| Examined Treatment | Total number of pollen treatments that were applied during the experiment |
|---|---|
| Every 3 days | 18 |
| Every week | 9 |
| Every 2 weeks | 5 |

On September 2-4 the experiment was harvested, namely all the above-ground material of each *A. palmeri* female plant was cut and was placed in large bags. All *A. palmeri* female plants were placed in the bag for drying in controlled growing rooms with 34° C./24° C. day/night conditions for at least 1 month. All the seeds from each *A. palmeri* female plant were harvested using the following procedure: i)Inflorescences from all spikes were harvested and placed in plastic boxes. ii) Seeds were threshed from the inflorescences using a rubbing apparatus that was built for that purpose. iii) Normal *A. palmeri* seeds were separated from debris+aborted *A. palmeri* seeds using seed blower machine (www(dot)Alibaba(dot)com/product-detail/CFY-II-Seed-Blower_60652162724.html?spm=a2700.7724838.2017115.21.1927367eRHQclq&s=p).

The separation procedure was conducted at low intensity of air blowing (approximately 10-15% of the maximal intensity of the machine) for a maximal duration of 5 minutes for each material batch. The amount of material for separation was placed inside the designated cup, up to 5 cm in height (therefore, the material was split to several batches when it was of higher volume than the designated amount). This separation was feasible as the weight of normal seeds is much higher than that of aborted seeds or the threshed debris. The total weight of seeds per *A. palmeri* female plant was weighed and the average and standard error of each treatment was calculated. In addition, a t-test for comparing the non-treated control to the all other treatments was performed. See all statistical information in the following Table 10.

TABLE 10

| | No-treatment control | Every 3 days treatment | Every week treatment | Every two weeks treatment |
|---|---|---|---|---|
| Average (g) | 17.15 | 10.42 | 13.80 | 6.70 |
| SE (g) | 3.09 | 1.18 | 1.92 | 0.92 |
| P-value of T-test | | 0.03458 | 0.33859 | 0.00037 |

Example 5

Achieve Increase in the Fraction of Aborted Seeds Following Artificial Pollination with X-Ray Irradiated *A. palmeri* Pollen in Net-House Conditions in Various Application Intervals The experiment was conducted during summer times in Rehovot, Israel. Sixteen female *A. palmeri* plants were arranged in a net house in a 4 boxes structure. Each box contained 4 *A. palmeri* female plants and a flowering male plant was placed in the middle. To allow competition from natural pollen shed from male plants.

Pollen for the treatments were collected from males that were grown in a separate location. The pollen was X-ray irradiated with a dose of 300 Gy and it was examined for it viability using TTC staining (Brown, 1954; Oberle & Watson, 1953; Norton, 1966) and in-vitro pollen tube germination (Shauck, PhD Thesis, University of Missouri 2014, Identification of nontarget-site mechanisms of glyphosate resistance in roots and pollen of *amaranthus* and *ambrosia*).

Four treatments were examined: No-treated control and three different artificial pollination regimens: i). Every week (total of 4 treatments). ii). Every 2 weeks (total of 2 treatments). And iii). Every 3 weeks (total of 2 treatments). All treatment regimens were randomly distributed in all 4 boxes. The artificial pollination was conducted using a pollen mini-duster machine (kiwi pollen mini-duster www(dot)kiwipollen(dot)com/dry-applicators/) for 15 seconds per female plant on speed 8. As the pollen was mixed with Talc in a ratio of 2:1 of pollen:Talc the amount of pollen that was spread per treated female plant per application was approximately 250 mg.

At the end of the experiment, 3 spikes were harvested from each *A. palmeri* female plant. Spikes were dried and all seeds were harvested manually. Normal seeds and aborted seeds were separated manually and the number of normal seeds and aborted seeds per spike were recorded. The values of the 3 spikes taken from each *A. palmeri* female plant were averaged to reduce noise and these averaged values were used for the statistical analysis of comparing the no-treated control with the 3 different treatment regimens. The average fraction of aborted seed, standard deviation and the p-value of t-test statistics are presented in the below Table 11 (separation between aborted seed vs. non-aborted seed was done based on morphology).

TABLE 11

| | Fraction of aborted seeds | | | |
|---|---|---|---|---|
| | Every 1 week | Every 2 weeks | Every 3 weeks | No-treated control |
| Average | 0.69 | 0.58 | 0.45 | 0.18 |
| SD | 0.20 | 0.12 | 0.09 | 0.12 |
| P-value of T-test vs. control | 0.0044 | 0.0034 | 0.0123 | |

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

It is the intent of the Applicant(s) that all publications, patents and patent applications referred to in this specification are to be incorporated in their entirety by reference into the specification, as if each individual publication, patent or patent application was specifically and individually noted when referenced that it is to be incorporated herein by reference. In addition, citation or identification of any reference in this application shall not be construed as an admission that such reference is available as prior art to the present invention. To the extent that section headings are used, they should not be construed as necessarily limiting. In addition, any priority document(s) of this application is/are hereby incorporated herein by reference in its/their entirety.

REFERENCES

Other References are Cited in the Application

1. Schnable and Wise. (1998). The molecular basis of cytoplasmic male sterility and fertility restoration. Trends in Plant Science. 3, 175-180.
2. Oerke, E-C. (2006) Crop losses to pests. J Agric. Sci. 144, 31-43
3. Pimentel, D. et al. (2000) Environmental and economic costs of nonindigenous species in the United States. BioScience 50, 53-65
4. Delye et al. (2013) Deciphering the evolution of herbicide resistance in weeds.
Trends in Genetics 29, 649-658
5. Klassen, W., C. F. Curtis (2005). History of the sterile insect technique, pp. 3-36 In V. A. Dyck, J. Hendrichs, and A. S. Robinson. The Sterile Insect Technique: Principles and Practice in Area-Wide Integrated Pest Management. Springer, Dordrecht, The Netherlands. 787 pp.

6. Yosiaki ITO et al. (2003) Eradication of the Melon Fly, Bactroceracucurbitae, from Okinawa, Japan, by Means of the Sterile Insect Technique, with Special Emphasis on the Role of Basic Studies, Journal of Asia-Pacific Entomology. 6, 119-129.
7. Kohama, T et al. (2003) A progress report on the eradication program of the sweet potato weevil, Cylasformicarius (Fabricius) (Coleoptera: Brentidae), with both male annihilation using sex pheromone and sterile insect releases in Kume Island, Okinawa, Japan, pp. 65-69. In Recent trends on sterile insect technique and area-wide integrated pest management—economic feasibility, control projects, farmer organization and Bactrocera *dorsalis* complex control study. Research Institute for Subtropics, Okinawa, Japan.
8. Pandey et al. (2006) Zinc is critically required for pollen function and fertilisation in lentil. Journal of Trace Elements in Medicine and Biology Volume 20, Issue 2, Pages 89-96
9. Bhalla et al. (2001) Reduction in allergenicity of grass pollen by genetic engineering. Int Arch Allergy Immunol. 124(1-3):51-4.
10. Sauer, J. D. (1972) The dioecious amaranths: a new species name and major range extensions. Madrono 21:426-434.
11. Ribeiro, D. N. et al. (2012) Apomixis involvement in inheritance of glyphosate resistance in *Amaranthus palmeri* from Mississippi. Abstracts of the Weed Science Society of America Annual Meeting. www(dot)wssaabstracts(dot)com/public/9/abstract-438(dot)html.
12. Schernthaner, J. P. et al. (2003) Control of seed germination in transgenic plants based on the segregation of a two-component genetic system. PNAS 100(11):6855-6859.
13. Gaines, T. A et al. (2012) Interspecific hybridization transfers a previously unknown glyphosate resistance mechanism in *Amaranthus* species. Evolutionary Applications 5(1):29-38.
14. Padidam et al. (2003) Chemically regulated gene expression in plants. Curr Opin Plant Biol. 6(2):169-77.
15. Hughes, D. W., and Galau, G. A. (1989) Temporally modular gene expression during cotyledon development, Genes and Development 3:358-369.
16. Horak M J et al. (1997) Control and cross-resistance of an acetolactate synthase inhibitor-resistant palmer amaranth (*Amaranthus palmeri*) biotype Weed Technology 11(1):p132
17. Patzoldt W L et al (2002). Variable herbicide response among Illinois waterhemp (*Amaranthus rudis* and *A. tuberculatus*) populations. Crop Prot 21: 707-712
18. Culpepper A S et al. (2006). Glyphosate-resistant Palmer amaranth (*Amaranthus palmeri*) confirmed in Georgia. Weed Science 54(4):620-626.
19. Agriculture Research Service National Plant Germplasm System plant introduction
20. Vijay K. et al. (2013) Glyphosate Resistance in Tall Waterhemp (*Amaranthus tuberculatus*) from Mississippi is due to both Altered Target-Site and Nontarget-Site Mechanisms. Weed Science 61(3):374-383.
21. Heap, I. The International Survey of Herbicide Resistant Weeds.
22. Matzrafi M and Baruch R (2015) Multiple herbicide resistance in rigid ryegrass (*Lolium Rigidum*) in Israel. The 6$^{th}$ international weed science congress.
23. Khraiwesh, B. et al. (2012) Role of miRNAs and siRNAs in biotic and abiotic stress responses of plants. Biochim Biophys Acta. 1819(2): 137-148
24. Santos-Mendoza et al., (2008) Deciphering gene regulatory networks that control seed development and maturation in *Arabidopsis*.
25. Pedrosa A M, et al., (2015) Late Embryogenesis Abundant (LEA) Constitutes a Large and Diverse Family of Proteins Involved in Development and Abiotic Stress Responses in Sweet Orange (*Citrus sinensis* L. Osb). 10(12). e0145785
26. Le B H et al., (2010) Global analysis of gene activity during *Arabidopsis* seed development and identification of seed-specific transcription factors. PNAS 26 107(18) 8063-8070.
27. McElver J et al., (2001) Insertional Mutagenesis of Genes Required for Seed Development in *Arabidopsis thaliana*. Genetics 159: 1751-1763.
28. Chen F, Bradford K J (2000) Expression of an expansin is associated with endosperm weakening during tomato seed germination. Plant Physiol. 124:1265-1274.
29. Nonogaki H, Gee O H, Bradford K J: A germination-specific endo R mannanase gene is expressed in the micropylar endosperm cap of tomato seeds. Plant Physiol 2000, 123:1235-1246.
30. Leubner-Metzger G, Meins F: Sense transformation reveals a novel role for class I β-1,3-glucanase in tobacco seed germination. Plant J 2000, 23:215-221. A functional analysis of the role of 1,3 glucanases in seed germination.
31. Wu C T, Leubner-Metzger G, Meins F, Bradford K J: Class I β-1,3,-glucanase and chitinase are expressed in the micropylar endosperm of tomato seeds prior to radicle emergence. Plant Physiol 2001, 126:1299-1313.
32. Toorop P E, van Aelst A C, Hilhorst H W M: The second step of the biphasic endosperm cap weakening that mediates tomato (*Lycopersicon esculentum*) seed germination is under control of ABA. J Exp Bot 2000, 51:1371-1379.
33. Dubreucq B, Berger N, Vincent E, Boisson M, Pettetier G, • Caboche M, Lepiniec L: The *Arabidopsis* AtERP1 extensin-like gene is specifically expressed in endosperm during seed germination. Plant J 2000, 23:643-652.
34. Shu K et al. (2015) Dormancy and germination: How does the crop seed decide? Plant Biolll04-1112:(6)17.
35. Jofre-Garfias, A E et al., (1997) *Agrobacterium*-mediated transformation of *Amaranthus hypochondriacus*: light- and tissue-specific expression of a pea chlorophyll a/b-binding protein promoter. Plant Cell Rep. 16, 847-852.
36. Swain et al., (2010)*Agrobacterium*×plant factors influencing transformation of 'Joseph's coat' (*Amaranthus tricolor* L.) Scientia Horticulturae 125:461-468.
37. Pal A. et al. (2013) *Agrobacterium* pRi TL-DNA rolB and TR-DNA Opine Genes Transferred to the Spiny Amaranth (*Amaranthus spinosus* L.), A Nutraceutical Crop, Food Technol. Biotechnol. 51 26-35.
38. Atkinson, N J and Urwin, PE (2012) The interaction of plant biotic and abiotic stresses: from genes to the field. J Exp Bot. 63(10):3523-3543.
39. Chen et al., (2004) The development of an *Arabidopsis* model system for genomewide analysis of polyploidy effects. Biol J Linn Soc Lond.; 82(4): 689-700.
40. Castro et al., (2003) Changes in allele frequencies in colchicines-treated ryegrass populations assessed with RAPD markers. Agrociencia 9: 107-112.
41. Soo Jeong Kwon et al., (2014) Tetraploid induction approach induced by colchicine of Prunella vulgaris for. albiflora Nakai. International Journal of Scientific and Research Publications, Volume 4, Issue 12, ISSN 2250-3153

42. Roselaine Cristina Pereira et al., (2014) Chromosome duplication in *Lolium multiflorum* Lam. Crop Breeding and Applied Biotechnology 14: 251-255
Terminator patent—U.S. Pat. No. 5,723,765
Reverse sterility patents—AU621195, U.S. Pat. No. 5,808, 034

What is claimed is:

1. A method of *Amaranthus* control, the method comprising:

artificially pollinating a population of plants of an *Amaranthus* species selected from the group consisting of *A. tuberculatus* and *A. palmeri* at a growth area with X-ray irradiated pollen of said *Amaranthus* species, wherein said artificially pollinating is under competition conditions with wild pollen of said *Amaranthus* species and is done in a regimen including:

an effective amount of said irradiated pollen comprising 1 mg to 1 gram per plant during the flowering season of said *Amaranthus* species;

1-10 applications during the flowering season of said *Amaranthus* species; or repeated applications spanning from daily applications to once every two months during the flowering season of said *Amaranthus* species, wherein said artificially pollinating is done using a precision tool which maps the precise position of said population of plants of said *Amaranthus* species at said growth area, and wherein said regimen of artificial pollination reduces fitness of said population of plants in comparison to a control population of plants of the same species not having been artificially pollinated with said X-ray irradiated pollen.

2. The method of claim 1, wherein said regimen comprises repeated applications spanning from weekly applications to once every two months during the flowering season of said *Amaranthus* species.

3. The method of claim 1, wherein said regimen comprises repeated applications spanning from two applications per week to once every two months during the flowering season of said *Amaranthus* species.

4. The method of claim 1, wherein said effective amount comprises 10 mg to 300 mg per plant.

* * * * *